US009492671B2

(12) United States Patent
O'Brien et al.

(10) Patent No.: US 9,492,671 B2
(45) Date of Patent: Nov. 15, 2016

(54) ACOUSTICALLY TRIGGERED THERAPY DELIVERY

(71) Applicant: Medtronic, Inc., Minneapolis, MN (US)

(72) Inventors: Richard J O'Brien, Hugo, MN (US); James K Carney, Roseville, MN (US); Can Cinbis, Salt Lake City, UT (US); Jonathan L Kuhn, Ham Lake, MN (US); Thomas A Anderson, New Hope, MN (US); Taylor R Anderson, Stevens Point, WI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/694,990

(22) Filed: Apr. 23, 2015

(65) Prior Publication Data

US 2015/0321016 A1    Nov. 12, 2015

Related U.S. Application Data

(60) Provisional application No. 61/989,123, filed on May 6, 2014.

(51) Int. Cl.
*A61N 1/00* (2006.01)
*A61N 1/372* (2006.01)
*A61N 1/362* (2006.01)
*A61N 1/365* (2006.01)
*A61N 1/39* (2006.01)

(52) U.S. Cl.
CPC ......... *A61N 1/37217* (2013.01); *A61N 1/3627* (2013.01); *A61N 1/36514* (2013.01); *A61N 1/3987* (2013.01); *A61N 1/365* (2013.01); *A61N 1/37205* (2013.01)

(58) Field of Classification Search
CPC ............... A61N 1/3627; A61N 1/365; A61N 1/36514; A61N 1/37205; A61N 1/37217; A61N 1/3987
See application file for complete search history.

(56) References Cited

U.S. PATENT DOCUMENTS

| 4,280,502 | A | 7/1981 | Baker, Jr. et al. |
| 4,343,311 | A | 8/1982 | Markowitz |
| 4,374,382 | A | 2/1983 | Markowitz |

(Continued)

FOREIGN PATENT DOCUMENTS

| EP | 1541191 | 6/2005 |
| EP | 2471452 A1 | 7/2012 |

(Continued)

OTHER PUBLICATIONS (PCT/US2015/029458) PCT Notification of Transmittal of the International Search Report and the Written Opinion of the International Searching Authority, mailed Aug. 25, 2015, 8 pages.

(Continued)

*Primary Examiner* — George Manuel
(74) *Attorney, Agent, or Firm* — Evans M. Mburu

(57) ABSTRACT

A medical device system is configured to sense a physiological signal by a first device and generate a control signal by the first device in response to the physiological signal. An acoustical emitting device is controlled by the first device to emit an acoustical trigger signal in response to the control signal. A second device detects the acoustical trigger signal and delivers an automatic therapy to a patient in response to detecting the acoustical trigger signal.

23 Claims, 16 Drawing Sheets

(56) References Cited

U.S. PATENT DOCUMENTS

| | | |
|---|---|---|
| 4,481,950 A | 11/1984 | Duggan |
| 4,543,955 A | 10/1985 | Schroeppel |
| 4,787,389 A | 11/1988 | Tarjan |
| 4,830,006 A | 5/1989 | Haluska et al. |
| 4,865,037 A | 9/1989 | Chin et al. |
| 5,113,859 A | 5/1992 | Funke |
| 5,117,824 A | 6/1992 | Keimel et al. |
| 5,139,020 A * | 8/1992 | Koestner et al. ............... 607/24 |
| 5,144,950 A | 9/1992 | Stoop et al. |
| 5,174,289 A | 12/1992 | Cohen |
| 5,193,539 A | 3/1993 | Schulman et al. |
| 5,255,692 A | 10/1993 | Neubauer et al. |
| 5,312,445 A | 5/1994 | Nappholz |
| 5,331,966 A | 7/1994 | Bennett et al. |
| 5,354,316 A | 10/1994 | Keimel |
| 5,402,070 A | 3/1995 | Shelton et al. |
| 5,411,535 A | 5/1995 | Fujii et al. |
| 5,545,186 A | 8/1996 | Olson et al. |
| 5,620,474 A | 4/1997 | Koopman |
| 5,683,426 A | 11/1997 | Greenhut et al. |
| 5,749,909 A | 5/1998 | Schroeppel et al. |
| 5,814,089 A | 9/1998 | Stokes et al. |
| 5,817,130 A | 10/1998 | Cox et al. |
| 5,855,593 A | 1/1999 | Olson et al. |
| 5,893,882 A | 4/1999 | Peterson et al. |
| 5,902,326 A | 5/1999 | Lessar et al. |
| 5,928,271 A | 7/1999 | Hess et al. |
| 5,954,649 A | 9/1999 | Chia et al. |
| 6,016,448 A | 1/2000 | Busacker et al. |
| 6,108,579 A | 8/2000 | Snell et al. |
| 6,206,847 B1 | 3/2001 | Edwards et al. |
| 6,208,894 B1 | 3/2001 | Schulman et al. |
| 6,256,534 B1 | 7/2001 | Dahl |
| 6,298,261 B1 | 10/2001 | Rex |
| 6,393,316 B1 | 5/2002 | Gillberg et al. |
| 6,442,426 B1 | 8/2002 | Kroll |
| 6,477,420 B1 | 11/2002 | Struble et al. |
| 6,505,067 B1 | 1/2003 | Lee |
| 6,508,771 B1 | 1/2003 | Padmanabhan et al. |
| 6,522,915 B1 | 2/2003 | Ceballos et al. |
| 6,526,311 B2 | 2/2003 | Begemann |
| 6,592,519 B1 | 7/2003 | Martinez |
| 6,622,046 B2 | 9/2003 | Fraley et al. |
| 6,628,989 B1 | 9/2003 | Penner et al. |
| 6,631,290 B1 | 10/2003 | Guck et al. |
| 6,738,668 B1 | 5/2004 | Mouchawar et al. |
| 6,754,528 B2 | 6/2004 | Bardy et al. |
| 6,760,615 B2 | 7/2004 | Ferek-Petric |
| 6,764,446 B2 | 7/2004 | Wolinsky et al. |
| 6,788,971 B1 | 9/2004 | Sloman et al. |
| 6,810,283 B2 | 10/2004 | Suribhotla |
| 6,904,315 B2 | 6/2005 | Panken et al. |
| 6,934,585 B1 | 8/2005 | Schloss et al. |
| 7,024,248 B2 | 4/2006 | Penner et al. |
| 7,027,858 B2 | 4/2006 | Cao |
| 7,160,258 B2 * | 1/2007 | Imran et al. ................... 600/593 |
| 7,181,284 B2 | 2/2007 | Burnes et al. |
| 7,198,603 B2 | 4/2007 | Penner et al. |
| 7,272,448 B1 | 9/2007 | Morgan et al. |
| 7,283,874 B2 | 10/2007 | Penner |
| 7,392,085 B2 | 6/2008 | Warren et al. |
| 7,532,929 B2 | 5/2009 | Mussig et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,630,767 B1 | 12/2009 | Poore et al. |
| 7,634,313 B1 | 12/2009 | Kroll et al. |
| 7,706,879 B2 | 4/2010 | Burnes et al. |
| 7,742,812 B2 | 6/2010 | Ghanem |
| 7,848,815 B2 | 12/2010 | Brisken et al. |
| 7,881,791 B2 | 2/2011 | Sambelashvili et al. |
| 7,890,173 B2 | 2/2011 | Brisken et al. |
| 7,904,153 B2 | 3/2011 | Greenhut et al. |
| 7,930,027 B2 | 4/2011 | Prakash et al. |
| 7,930,031 B2 | 4/2011 | Penner |
| 7,937,148 B2 | 5/2011 | Jacobson |
| 7,941,218 B2 | 5/2011 | Sambelashvili et al. |
| 7,945,064 B2 | 5/2011 | O'Brien, Jr. et al. |
| 7,953,493 B2 | 5/2011 | Fowler et al. |
| 7,991,467 B2 | 8/2011 | Markowitz et al. |
| 7,996,087 B2 | 8/2011 | Cowan et al. |
| 8,002,718 B2 | 8/2011 | Buchholtz et al. |
| 8,032,219 B2 | 10/2011 | Neumann et al. |
| 8,095,207 B2 | 1/2012 | Belalcazar |
| 8,145,308 B2 | 3/2012 | Sambelashvili et al. |
| 8,160,684 B2 | 4/2012 | Ghanem et al. |
| 8,160,686 B2 | 4/2012 | Allavatam et al. |
| 8,204,590 B2 | 6/2012 | Sambelashvili et al. |
| 8,214,041 B2 | 7/2012 | Van Gelder et al. |
| 8,275,432 B2 | 9/2012 | Kuhn et al. |
| 8,315,701 B2 | 11/2012 | Cowan et al. |
| 8,352,025 B2 | 1/2013 | Jacobson |
| 8,364,276 B2 | 1/2013 | Willis |
| 8,391,964 B2 | 3/2013 | Musley et al. |
| 8,428,716 B2 | 4/2013 | Mullen et al. |
| 8,433,409 B2 | 4/2013 | Johnson et al. |
| 3,452,402 A1 | 5/2013 | Ecker et al. |
| 8,457,742 B2 | 6/2013 | Jacobson |
| 8,521,268 B2 | 8/2013 | Zhang et al. |
| 8,532,785 B1 | 9/2013 | Crutchfield et al. |
| 8,538,524 B2 | 9/2013 | Rosenberg |
| 8,540,631 B2 | 9/2013 | Penner et al. |
| 8,541,131 B2 | 9/2013 | Lund et al. |
| 8,617,082 B2 | 12/2013 | Zhang et al. |
| 8,639,333 B2 | 1/2014 | Stadler et al. |
| 8,652,048 B2 | 2/2014 | Skerl et al. |
| 8,666,505 B2 | 3/2014 | O'Brien et al. |
| 8,718,773 B2 | 5/2014 | Willis et al. |
| 8,718,793 B2 | 5/2014 | O'Connor |
| 8,744,572 B1 | 6/2014 | Greenhut et al. |
| 8,768,459 B2 | 7/2014 | Ghosh et al. |
| 8,886,307 B2 | 11/2014 | Sambelashvili et al. |
| 8,886,311 B2 | 11/2014 | Anderson et al. |
| 8,923,963 B2 | 12/2014 | Bonner et al. |
| 9,008,776 B2 | 4/2015 | Cowan et al. |
| 9,168,380 B1 | 10/2015 | Greenhut et al. |
| 2004/0204744 A1 | 10/2004 | Penner et al. |
| 2004/0215308 A1 | 10/2004 | Bardy et al. |
| 2005/0010120 A1 | 1/2005 | Jung |
| 2005/0043761 A1 | 2/2005 | Connelly et al. |
| 2005/0277990 A1 | 12/2005 | Ostroff et al. |
| 2006/0009818 A1 | 1/2006 | Von Arx et al. |
| 2006/0085041 A1 | 4/2006 | Hastings et al. |
| 2006/0116593 A1 | 6/2006 | Zhang |
| 2006/0161205 A1 | 7/2006 | Mitrani et al. |
| 2006/0235478 A1 | 10/2006 | Van Gelder et al. |
| 2006/0241705 A1 | 10/2006 | Neumann et al. |
| 2007/0049975 A1 | 3/2007 | Cates et al. |
| 2007/0088394 A1 | 4/2007 | Jacobson |
| 2007/0088398 A1 | 4/2007 | Jacobson |
| 2007/0293900 A1 | 12/2007 | Sheldon et al. |
| 2007/0299475 A1 | 12/2007 | Levin et al. |
| 2008/0119911 A1 | 5/2008 | Rosero |
| 2008/0154322 A1 | 6/2008 | Jackson et al. |
| 2008/0269816 A1 | 10/2008 | Prakash et al. |
| 2008/0269823 A1 | 10/2008 | Burnes et al. |
| 2008/0288039 A1 | 11/2008 | Reddy |
| 2009/0036940 A1 | 2/2009 | Wei et al. |
| 2009/0036941 A1 | 2/2009 | Corbucci |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0042108 A1 | 2/2010 | Hibino |
| 2010/0106210 A1 | 4/2010 | Hedberg et al. |
| 2010/0152798 A1 | 6/2010 | Sanghera et al. |
| 2010/0198291 A1 | 8/2010 | Sambelashvili et al. |
| 2010/0228308 A1 | 9/2010 | Cowan et al. |
| 2010/0286541 A1 | 11/2010 | Musley et al. |

(56) References Cited

U.S. PATENT DOCUMENTS

| | | |
|---|---|---|
| 2011/0071586 A1 | 3/2011 | Jacobson |
| 2011/0125078 A1 | 5/2011 | Denison et al. |
| 2011/0184492 A1 | 7/2011 | Martens et al. |
| 2011/0190841 A1 | 8/2011 | Sambelashvili et al. |
| 2011/0196444 A1 | 8/2011 | Prakash et al. |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0172892 A1 | 7/2012 | Grubac et al. |
| 2012/0263218 A1 | 10/2012 | Dal Molin et al. |
| 2012/0296228 A1 | 11/2012 | Zhang et al. |
| 2012/0303084 A1 | 11/2012 | Kleckner et al. |
| 2012/0316613 A1 | 12/2012 | Keefe et al. |
| 2013/0013017 A1 | 1/2013 | Mullen et al. |
| 2013/0066169 A1 | 3/2013 | Rys et al. |
| 2013/0103109 A1 | 4/2013 | Jacobson |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0138006 A1 | 5/2013 | Bornzin |
| 2013/0197599 A1 | 8/2013 | Sambelashvili et al. |
| 2013/0226259 A1 | 8/2013 | Penner |
| 2013/0231710 A1 | 9/2013 | Jacobson |
| 2013/0268017 A1 | 10/2013 | Zhang et al. |
| 2013/0274828 A1 | 10/2013 | Willis |
| 2013/0282073 A1 | 10/2013 | Cowan et al. |
| 2014/0114372 A1 | 4/2014 | Ghosh et al. |
| 2014/0257421 A1 | 9/2014 | Sanghera et al. |
| 2014/0330208 A1 | 11/2014 | Christie et al. |
| 2014/0330326 A1 | 11/2014 | Thompson-Naumann et al. |
| 2014/0358135 A1 | 12/2014 | Sambelashvili et al. |
| 2015/0142070 A1 | 5/2015 | Sambelashvili |
| 2016/0113536 A1 | 4/2016 | Greenhut et al. |

FOREIGN PATENT DOCUMENTS

| | | |
|---|---|---|
| WO | 95/02995 | 2/1995 |
| WO | 03003905 | 1/2003 |

OTHER PUBLICATIONS (PCT/US2015/029464) PCT Notification of Transmittal of the International Search Report and the Written Opinion of the International Searching Authority, Mailed Jul. 13, 2015, 9 pages.

U.S. Appl. No. 13/665,601 to Bonner et al., entitled, "Leadless Pacemaker System," filed Oct. 31, 2012.

U.S. Appl. No. 14/261,460, filed Apr. 25, 2014, entitled "Implantable Medical Device System Having Implantable Cardiac Defibrillator System and Substernal Leadless Pacing Device".

U.S. Appl. No. 14/257,462, filed Apr. 21, 2014 entitled "Anchoring an Implantable Medical Device Within a Substernal Space".

(PCT/US2014/036782) PCT Notification of Transmittal of the International Search Report and the Written Opinion of the International Searching Authority, Mailed Aug. 22, 2014, 12 pages.

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

(PCT/US2014/066792) PCT Notification of Transmittal of the International Search Report and the Written Opinion of the International Searching Authority.

(PCT/US2013/013601) PCT Notification of Transmittal of the International Search Report and the Written Opinion of the International Searching Authority.

Rodney Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

U.S. Appl. No. 14/801,049, filed Jul. 16, 2015.

(PCT/US2015/029495) PCT Notification of Transmittal of the International Search Report and the Written Opinion of the International Searching Authority, mailed Aug. 12, 2015, 9 pages.

* cited by examiner

ACOUSTICALLY TRIGGERED THERAPY DELIVERY

REFERENCE TO RELATED APPLICATIONS

This application claims priority to U.S. Pat. Application No. 61/989,123 filed provisionally on May 6, 2014 and incorporated herein by reference in its entirety. This application also cross-references U.S. Pat. Application No. 61/989,114 and U.S. Pat. Application No. 61/989,302, filed provisionally on May 6, 2014; and U.S. patent application Ser. No. 14/695,013 and U.S. patent application Ser. No. 14/695,004, filed on even date herewith, all of which are incorporated herein by reference in their entirety.

TECHNICAL FIELD

The disclosure relates to an implantable medical device system and associated method for delivering a therapy using an acoustically-triggered therapy delivery device.

BACKGROUND

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, leadless intracardiac pacemakers have been introduced which can be implanted directly in a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of a leadless, intracardiac pacemaker.

New challenges arise, however, in controlling an intracardiac pacemaker to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in whom one or more heart chambers are electrically paced to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g., an atrio-ventricular (AV) interval and/or an inter-ventricular (VV) interval. The AV interval controls the timing of ventricular pacing pulses relative to an atrial depolarization, intrinsic or paced. The VV interval controls the timing of a pacing pulse in one ventricle relative to a preceding paced or intrinsic sensed event in the other ventricle. Pacing may be delivered in the right ventricle (RV) and/or the left ventricle (LV) to restore ventricular synchrony.

SUMMARY

In general, the disclosure is directed to an implantable medical device (IMD) system including a therapy delivery device and a sensing device and an associated method for triggering the therapy delivery device to deliver therapy. The sensing device senses a physiological signal to determine a need for therapy and generates a control signal passed to an acoustical trigger signal emitting device when therapy delivery by the therapy delivery device is required. The acoustical trigger signal emitting device emits an acoustical trigger signal that is detected by the therapy delivery device. In response to detecting the acoustical trigger signal, the therapy delivery device delivers at least a portion of a therapy.

In one example, the disclosure provides a medical device system for automatically delivering a therapy comprising a first device configured to sense a physiological signal and generate a control signal in response to the physiological signal, an acoustical emitting device controlled by the first device to emit an acoustical trigger signal in response to receiving the control signal from the first device, and a second device comprising a transducer for receiving the acoustical trigger signal. The second device is configured to detect the acoustical trigger signal and deliver a therapy to a patient in response to detecting the acoustical trigger signal.

In another example, the disclosure provides a method for delivering an automatic therapy by a medical device system comprising sensing a physiological signal by a first device, generating a control signal by the first device in response to the physiological signal, automatically emitting an acoustical trigger signal by an acoustical emitting device configured to receive the control signal, detecting the acoustical trigger signal by a second device comprising a transducer that is responsive to the acoustical trigger signal and delivering the therapy to a patient in response to the second device detecting the acoustical trigger signal.

In yet another example, the disclosure provides a non-transitory, computer-readable storage medium storing a set of instructions that, when executed by an implantable medical device system, cause the system to sense a physiological signal by a first device, generate a control signal by the first device in response to the physiological signal, emit an acoustical trigger signal by an acoustical emitting device in response to the control signal, detect the acoustical trigger signal by a second device comprising a transducer that is responsive to the acoustical trigger signal, and deliver a therapy by the second device to a patient in response to the second device detecting the acoustical trigger signal.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
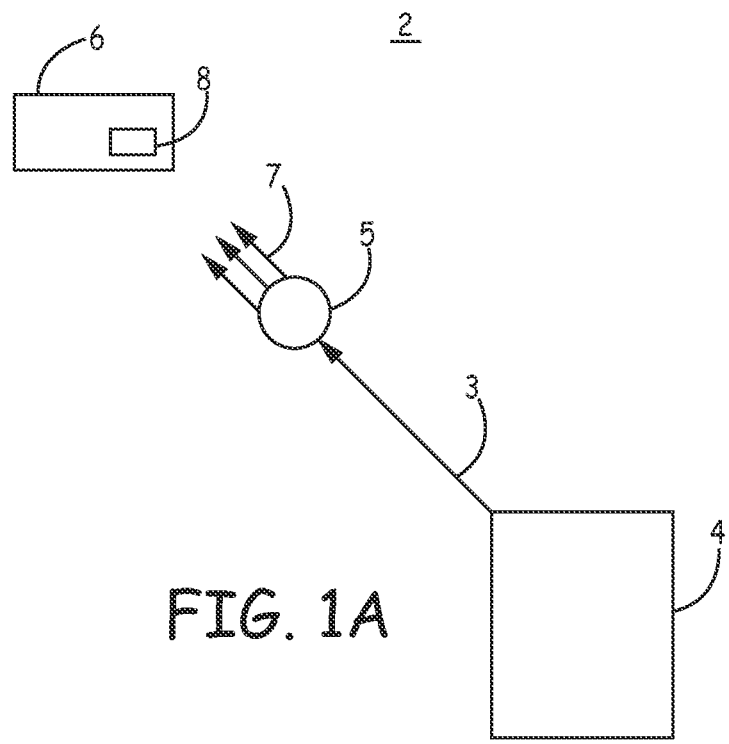
FIG. 1A is a conceptual diagram of an implantable medical device (IMD) system including an acoustically-triggered therapy delivery device.

IMD systems and associated techniques are disclosed herein for sensing physiological signals using a sensing device implanted at one location and triggering a therapy delivery device to deliver an automatic therapy to a targeted patient tissue at a second location. The therapy delivery device is triggered to deliver the therapy by an acoustical trigger signal transmitted by a piezoelectric device that is controlled by the sensing device. Automatic therapy delivery is achieved by the separate sensing and therapy delivery devices without requiring the two devices to be physically connected to each other. Among other things, elimination of the physical connection between the sensing and therapy delivery components of an IMD system enables minimally invasive implant procedures to be used, down-sizing of IMD system components, and/or elimination of some components such as medical leads, sensing capability in the therapy delivery device, and a radio frequency (RF) amplifier and transceiver in the therapy delivery device.

As used herein, a "trigger signal" is an acoustical signal, e.g., an ultrasonic signal, emitted by an acoustical transducer when an electrical signal is applied to the transducer. The acoustical trigger signal is a command signal, which is generated by and sent from the sensing device to the therapy delivery device via an emitting device using acoustic energy as a means of communication, to trigger the delivery of therapy by the therapy delivery device upon detection of the trigger signal.

A "triggered therapy delivery device" as used herein is a device that is triggered by the trigger signal to deliver a therapy to a targeted patient tissue. In the illustrative embodiments described herein, the therapy is an electrical stimulation therapy, such as cardiac pacing pulses, though other types of therapy, such as drug delivery, are contemplated. The triggered therapy delivery device includes a transducer that produces an electrical signal in response to being subjected to the trigger signal. The electrical signal is compared to a trigger detection threshold and causes the therapy delivery device to deliver a therapeutic stimulation pulse to a targeted tissue of the patient when the detection threshold is exceeded. The "triggered therapy delivery device" as disclosed herein, therefore, is not making a decision to deliver therapy based on processing of a physiological signal sensed using an acoustic transducer that produces a time-varying signal waveform, such as a blood pressure signal or a heart sound signal, that is correlated to a physiological condition or physiological events. The decision to deliver therapy is made by the sensing device that is controlling the transducer that emits the trigger signal. The sensing device and the therapy delivery device need not be in wired connection with each other.

FIG. 1 is a conceptual diagram of an IMD system 2 including an acoustically-triggered therapy delivery device. System 2 includes a sensing device 4, an acoustical signal emitting device 5, and a therapy delivery device 6. Sensing device 4 is capable of sensing a physiological signal for determining when a therapy is needed. Sensing device 4 may or may not be capable of delivering a therapy directly to the patient. Sensing device 4 is at least capable of sensing a physiological signal, determining need for therapy based on the physiological signal, and producing a control signal 3 passed to emitting device 5. In various examples, sensing device 4 may be a pacemaker, ICD, ECG monitor, hemodynamic monitor, neurostimulator, drug pump, or other IMD.

Sensing device 4 is in wired or wireless communication with acoustical signal emitting device 5. Sensing device 4 sends a control signal 3 to emitting device 5 to cause emitting device 5 to emit an acoustical trigger signal 7, shown as a directionally focused signal in FIG. 1. In other embodiments, acoustical trigger signal 7 may be multi-directional (e.g., non-focused).

In the diagram, emitting device 5 is shown as a separate device from sensing device 4, however in some examples emitting device 5 is incorporated in sensing device 4. In some applications, sensing device 4 incorporating emitting device 5 may be implanted (or located externally) at a location that is within an acoustical trigger signal receiving range of therapy delivery device 6. In other applications, the physical locations of sensing device 4 and therapy delivery device 6 may be too far apart or separated by highly reflective tissues or sound attenuating structures that would prohibit reliable reception of an acoustical trigger signal by therapy delivery device 6. In these situations, the emitting device 5 is located at a spaced apart location from sensing device 4 and positioned to reliably transmit an acoustical trigger signal to therapy delivery device 6.

In various embodiments, sensing device 4 may sense any physiological signal or combination of signals used in a particular application for determining a need for therapy. Such signals may include, but are not limited to, an electrical signal such as an ECG (electrocardiogram), EGM (cardiac electrogram), EMG (electromyogram), EEG (electroencephalogram) or nerve action potentials. Additionally or alternatively, sensing device 4 may be configured to sense a mechanical or chemical physiological signal. Other physiological signals that may be sensed by sensing device 4 include, without limitation, a blood or other pressure signal, an optical signal such as an optical signal used to determine blood or tissue oxygen saturation, an acoustical signal such as heart sounds, an activity signal, or a posture signal.

The physiological signals may be used to control the time that therapy delivery device 6 is triggered to deliver therapy relative to sensed physiological events and/or determine a need for therapy delivery based on a state or condition determined from the physiological signal(s) sensed by sensing device 4. As such, sensing device 4 is configured to determine a time that therapy is needed according to programmed therapy delivery algorithms and therapy delivery control parameters for a given application.

When sensing device 4 determines that it is time for a therapy to be delivered, a control signal 3 is passed to acoustical signal emitting device 5. Emitting device 5 may be physically coupled to sensing device 4 by a medical lead for passing the control signal as an electrical signal to emitting device 5. Alternatively, emitting device 5 may be configured to receive wireless telemetry communication signals from sensing device 4, such as a radio frequency (RF) command signal that causes emitting device 5 to emit acoustical trigger signal 7.

Therapy delivery device 6 includes an acoustic receiver 8, which includes a transducer that receives the acoustical trigger signal 7 and coverts it to an electrical signal. The electrical signal is compared to a threshold to detect the acoustical trigger signal 7. In response to detecting the acoustical trigger signal 7, therapy delivery device 6 delivers a therapy, such as one or more electrical stimulation pulses.

An "acoustical trigger signal" as used herein refers to a vibrational signal produced by an acoustical transducer in emitting device 5 and received by an acoustical transducer 8 in the receiving therapy delivery device 6. The acoustical trigger signal 7 is not a sensed physiological signal that is produced, for example, by vibrations of the patient's heart, muscle, lungs, or other body part acting on a transducer. The acoustical trigger signal 7 is produced when a control signal 3, such as a logic signal, is produced by the circuitry of the sensing device 4. The control signal 3 may be generated based on physiological signals sensed by the sensing device 4, however, the acoustical trigger signal itself is originated by a device-generated electrical signal activating an acoustical transducer of the emitting device 5, not a physiological motion or vibration acting on the transducer of emitting device 5 or on the therapy delivery device receiving transducer 8. In some embodiments, the acoustical trigger signal 7 can be referred to as a "pace trigger signal" because it is a pace timing signal that is emitted to set the timing of a pacing pulse. The acoustical trigger signal 7 may be separated in time from one or both of a sensed physiological event and a pacing pulse that is being delivered in a timed relation with the physiological event.

Therapy delivery device 6 is generally a miniaturized device that is adapted for implantation at a targeted therapy delivery site. In some applications, the target therapy delivery site requires a minimized device size in order to avoid complications, minimize patient discomfort, and/or facilitate minimally invasive implantation procedures. As such, therapy delivery device 6 may have reduced functionality for sensing physiological signals, data collection, radio frequency or other bi-directional telemetry communication, or other functions that may normally be present in a pacemaker, ICD, neurostimulator or other types of IMDs configured to automatically deliver a therapy to a patient.

For example, therapy delivery device 6 may be a transcatheter pulse generator having electrodes positioned along the housing of the therapy delivery device 6. In other examples, a short lead carrying one or more electrodes may extend from device 6. In illustrative embodiments described in greater detail below, the therapy delivery device 6 is a transcatheter, intracardiac pacemaker that is triggered by an acoustical trigger signal from emitting device 5 to deliver one or more cardiac pacing pulses. As used herein, a "transcatheter" pacemaker (or other transcatheter device) is a device that can be implanted at a target location via a catheter or other elongated, tubular delivery tool to advance the device to a target location without necessarily having direct line of sight at the target location. Therapy delivery device 6 is not limited to being a cardiac pacemaker. Device 6 may be embodied as other types of electrical stimulation therapy delivery devices, such as devices configured for delivering electrical stimulation to any excitable tissue, including the central nervous system, peripheral nervous system, smooth muscle tissue and/or skeletal muscle tissue.

Furthermore, it is recognized that therapy delivery device 6 triggered by acoustical trigger signal 7 to deliver therapy is not limited to being an electrical stimulation therapy delivery device. In alternative embodiments, therapy delivery device 6 may be configured to deliver other types of therapies using mechanical, optical, pharmaceutical or other therapeutic means. For example, therapy delivery device 6 may be a fluid delivery device for delivering a drug or biological agent.

Figure 1B:
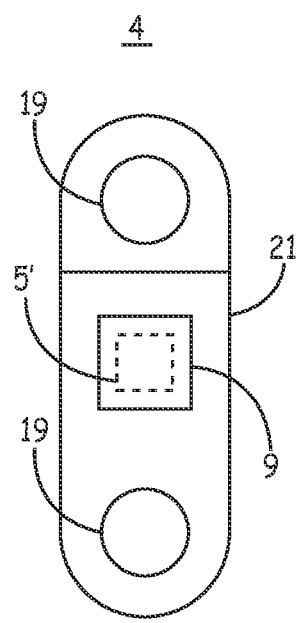
FIG. 1B is a conceptual diagram of a sensing device that may be included in an IMD system for triggering an acoustically-triggered therapy delivery device.

FIG. 1B is a conceptual diagram of one example of sensing device 4 that may be included in the IMD system 2 of FIG. 1A for triggering an acoustically-triggered therapy delivery device 6. The sensing device 4 may or may not include therapy delivery capabilities. In the example of FIG. 1B, sensing device 4 is a sensing-only device that sends acoustical trigger signals to therapy delivery device 8 to achieve therapy delivery. A "sensing-only" device is a device that senses one or more physiological signals to determine a need for therapy but does not deliver therapy directly to a targeted patient tissue.

Sensing device 4 may include a pair of sensing electrodes 19 along uninsulated portions of a conductive housing 11. Housing 11 may be formed of titanium, for example, and includes a thin foil membrane portion 9 that acoustically couples emitted signals with adjacent tissue. Emitting device 5' is provided as a housing-based emitting device that is positioned within housing 11 along foil membrane 9. Emitting device 5' may include one or more acoustical transducers, for example a two dimensional array of acoustical transducers, for transmitting a trigger signal through membrane 9 and adjacent tissue to therapy delivery device 6. The thickness of foil member 9 is selected to efficiently couple an emitted acoustical signal from emitting device 5' to adjacent tissue.

In one example, sensing device 4 may be positioned subcutaneously in a parasternal location for sensing ECG signals of a patient's heart via electrodes 19. Therapy delivery device 6 may be an intracardiac pacemaker implanted in a heart chamber. Sensing device 4 transmits acoustical trigger signals from emitting device 5' to therapy delivery device 6 to trigger therapy delivery device 6 to deliver one or more pacing pulses. In this way, a cardiac pacing system is provided including two minimally sized implantable devices, without requiring transvenous leads. The cardiac pacing system 2 may be a leadless medical device system in some examples.

Figure 2A:
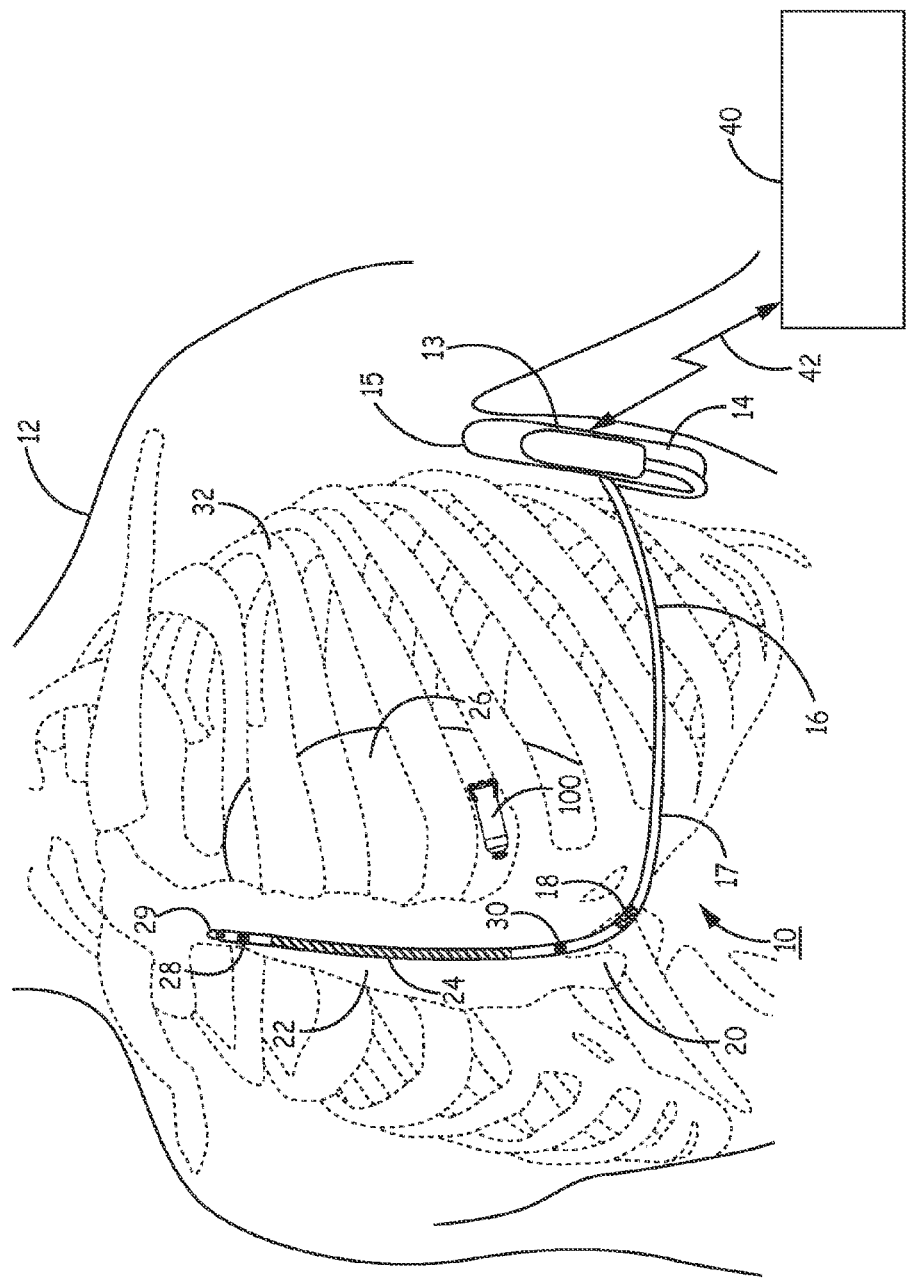
FIG. 2A is a conceptual diagram illustrating an (IMD) system that may be used to sense cardiac electrical signals in a patient and provide therapy to the patient's heart using an acoustically-triggered therapy delivery device.

FIG. 2A is a conceptual diagram illustrating an implantable medical device (IMD) system 10 that may be used to sense cardiac electrical signals in patient 12 and provide therapy to heart 26. IMD system 10 includes an intracardiac pacemaker 100 and an ICD 14 coupled to an extravascular defibrillation lead 16. Defibrillation lead 16 includes a defibrillation electrode 24, which may be an elongated coil electrode, a pair of sensing electrodes 28 and 30, and an acoustical signal emitting device 18. Electrodes 28 and 30 are illustrated as ring electrodes but may be or other types of electrodes, or combinations of electrodes. Acoustical signal emitting device 18 includes an acoustical transducer that is controlled by ICD 14 to emit acoustical trigger signals to cause pacemaker 100 to deliver one or more pacing pulses.

ICD 14 is shown implanted subcutaneously on the left side of patient 12. Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is offset laterally to the left or right side of the body of sternum 22 and may be implanted subcutaneously, e.g., between the skin and the ribs or sternum. Defibrillation lead 16 may be implanted at other locations or angles relative to sternum 22 or positioned further superior or inferior depending on the location of ICD 14, position of electrodes 24, 28, and 30 and acoustical signal emitting device 18 along lead 16 and the location of pacemaker 100, or other factors. In other instances, lead 16 may be implanted at other extravascular locations. In one example, lead 16 may be implanted at least partially in a substernal location or within ribcage 32, within the thoracic cavity and within or outside the pericardium, not necessarily in direct contact with heart 26.

Defibrillation lead 16 is positioned such that a therapy vector between defibrillation electrode 24 and a second electrode (such as a portion of the housing 15 of ICD 14 or an electrode placed on a second lead) is substantially across one or both ventricles of heart 26. The therapy vector may, in one example, be viewed as a line that extends from a point on the defibrillation electrode 24 to a point on the housing 15 (sometimes referred to as a "can" electrode) of ICD 14. In another example, defibrillation lead 16 may be placed along sternum 22 such that a therapy vector between defibrillation electrode 18 and housing 15 (or other electrode) is substantially across an atrium of heart 26. In this case, system 10 may be used to provide atrial therapies, such as therapies to treat atrial fibrillation.

Acoustical signal emitting device 18 is positioned to establish an acoustical signal transmission pathway that does not excessively attenuate the acoustical trigger signal transmitted from emitting device 18 to a receiver included in intracardiac pacemaker 100. For example, the location of emitting device 18 may be selected so that a direct acoustical pathway between emitting device 18 and pacemaker 100 avoids lung or other tissue that is a poor acoustic conductor, as much as possible. When lead 16 is positioned extrathoracically, emitting device 18 may be positioned inferior to the xyphoid process 20 in a position approximately as shown. In other examples, emitting device 18 is positioned relative to pacemaker 100 to establish an efficient sound transmission pathway, which may be a direct or indirect pathway that takes into account the acoustical properties of the surrounding and intervening tissues.

Defibrillation lead 16 may also include an attachment feature 29 at or toward the distal end of lead 16. The attachment feature 29 may be a loop, link, suture or other attachment feature useful to aid in implantation of lead 16 and/or for securing lead 16 to a desired implant location. In some instances, defibrillation lead 16 may include a fixation mechanism in addition to or instead of the attachment feature 29. For example, defibrillation lead 16 may include a suture sleeve or other fixation mechanism (not shown) located proximal to electrode 30 or near emitting device 18 that is configured to fixate lead 16 near the xiphoid process 20 or lower sternum location. The fixation mechanism (e.g., suture sleeve or other mechanism) may be integral to the lead or may be added by the user prior to implantation. The fixation mechanism may be used to stably locate emitting device 18 inferior to the xyphoid process 20, along an intercostal space, or other desired location to prevent rotation or shifting of the emitting device 18 that may cause trigger signal misdirection or trigger signal loss due to interference or attenuation by body tissues.

Although ICD 14 is illustrated as being implanted near a midaxillary line of patient 12, ICD 14 may be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 22. When the ICD 14 is implanted in the pectoral region, the system 10 may include a second lead including a defibrillation electrode, and optionally acoustical emitting device 18, that extends along the left side of the patient such that the defibrillation electrode of the second lead is located along the left side of the patient to function as an anode or cathode of the therapy vector for defibrillating heart 26.

ICD 14 includes a housing 15 that forms a hermetic seal that protects components within ICD 14. The housing 15 of ICD 14 may be formed of a conductive material, such as titanium or other biocompatible conductive material or a combination of conductive and non-conductive materials. Housing 15 may enclose one or more components, including processors, memories, transmitters, receivers, sensors, sensing circuitry, therapy circuitry and other appropriate components (often referred to herein as modules). In some instances, the housing 15 functions as an electrode (sometimes referred to as a "housing electrode" or "can electrode") that is used in combination with one of electrodes 24, 28 and 30 to deliver a therapy to heart 26 or to sense electrical activity of heart 26.

ICD 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing 15. Depending on the intended implant location of ICD 14, an acoustical signal emitting device may be included in connector assembly 13 and/or housing 15 in addition to or in place of the emitting device 18 carried by lead 16 for transmitting acoustical trigger signals to pacemaker 100. For example, an acoustical emitting device can be located within housing 15 along a thin foil membrane acting as an acoustical interface between the tissue and piezoelectric transducer included within housing 15 (e.g., as generally shown in FIG. 1B).

Lead 16 may include a connector at the proximal end of lead 16, such as a DF4 connector, bifurcated connector (e.g., DF-1/IS-1 connector), or other type of connector having at least one terminal pin that couples to a port within the connector assembly 13 of ICD 14. The lead body 17 of defibrillation lead 16 may be formed from a non-conductive material, including silicone, polyurethane, fluoropolymers, mixtures thereof, and other appropriate materials, and shaped to form one or more lumens within which the one or more elongated conductors extend.

Defibrillation lead 16 includes elongated electrical conductors (not illustrated) that each extend within the elongated lead body 17 from the connector on the proximal end of defibrillation lead 16 to respective electrodes 24, 28 and 30 and emitting device 18. Although defibrillation lead 16 is illustrated as including three electrodes 24, 28 and 30, defibrillation lead 16 may include more or fewer electrodes. When the connector of defibrillation lead 16 is connected to connector assembly 13, the respective conductors may electrically couple to circuitry, such as a therapy delivery module, a sensing module, or a trigger signal drive signal circuit of ICD 14 via connections in connector assembly 13, including associated feedthroughs.

The electrical conductors transmit electrical stimulation pulses from a therapy module within ICD 14 to one or more of electrodes 24, 28 and 30 and transmit sensed electrical signals from one or more of electrodes 24, 28 and 30 to the sensing module within ICD 14. An electrical conductor extending from the proximal lead connector to emitting device 18 conducts a drive signal to emitting device 18 to cause emitting device 18 to emit an acoustical trigger signal at appropriate times for causing intracardiac pacemaker 100 to deliver one or more pacing pulses to heart 26.

ICD 14 is configured to sense cardiac electrical signals via one or more sensing vectors that include combinations of electrodes 28 and 30 and housing 15. For example, ICD 14 may obtain cardiac electrical signals using a sensing vector between electrodes 28 and 30, between electrode 28 and housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and housing 15.

ICD 14 determines a need for pacing therapy in response to the sensed cardiac electrical signals, which may include P-waves and R-waves for example, and controls emitting device 18 to emit acoustical trigger signals based on that determination. The need for pacing pulses may be determined according to programmed single chamber, dual chamber or multi-chamber bradycardia or CRT control parameters or other cardiac pacing therapy parameters. ICD 14 may also analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 24 and the housing 15.

Electrodes 24, 28, 30 and housing 15 may be used for sensing ECG signals for use in controlling the timing of an R-wave synchronized shock delivered by ICD 14 as well as for controlling timing of pacing pulses delivered by pacemaker 100. In some instances, one or more pacing therapies may be delivered prior to or after delivery of a defibrillation shock by ICD 14, such as anti-tachycardia pacing (ATP) or post-shock pacing. In these instances, ICD 14 may generate and deliver pacing pulses via therapy vectors that include electrodes 24, 28, 30, and/or housing 15. Alternatively, ICD 14 causes acoustical signal emitting device 18 to emit trigger signals to cause pacemaker 100 to deliver pacing pulses to heart 26 at appropriate times when ATP or post-shock pacing is needed as well as bradycardia or CRT pacing therapy is needed.

The example illustrated in FIG. 2A is illustrative in nature and should not be considered limiting of the type of sensing device used in a triggered therapy delivery system and the techniques described herein. For instance, in addition to sensing ECG signals, ICD 14 may include shock therapy capabilities only without pacing therapy capabilities. In other examples, ICD 14 may be coupled to more than one lead for sensing ECG signals and/or sending trigger signals to pacemaker 100. In other examples, a sensing device may be substituted for ICD 14 that is a single chamber or dual chamber subcutaneous pacemaker without cardioversion/defibrillation capabilities or a sensing-only device without therapy delivery capabilities, e.g., as shown in FIG. 1B. Any of these sensing devices may be coupled to housing-based electrodes and/or electrodes carried by a transvenous, intracardiac or extravascular, extracardiac lead for sensing a cardiac electrical signal and determining appropriate times for triggering pacemaker 100 to delivery therapy.

Pacemaker 100 is a transcatheter intracardiac pacemaker adapted for implantation wholly within a heart chamber, e.g., wholly within the RV, wholly within the LV, wholly within the right atrium (RA) or wholly within the left atrium (LA) of heart 26. In the example of FIG. 2A, pacemaker 100 is positioned proximate to an inner wall of the LV to provide left ventricular pacing. In other examples, pacemaker 100 is positioned proximate to an inner wall of the right ventricle to provide right ventricular pacing. In other examples, pacemaker 100 may be positioned at any other location outside or within heart 26, including epicardial locations. For example, pacemaker 100 may be positioned outside or within the right atrium or left atrium, e.g., to provide respective right atrial and left atrial pacing. In other embodiments, pacemaker 100 may be embodied as a therapy delivery device for delivering an electrical stimulation therapy at another body location. Pacemaker 100 is shown as a leadless device in FIG. 2A. It is contemplated, however that in other embodiments pacemaker 100 may be coupled to a lead or extension extending from pacemaker 100 to position therapy delivery electrodes at a location spaced apart from pacemaker 100.

Depending on the implant location, pacemaker 100 may be configured to deliver an electrical stimulation therapy to target therapy site(s) other than the myocardium. For example, pacemaker 100 may provide atrioventricular nodal stimulation, fat pad stimulation, vagal stimulation, or other types of neurostimulation. In other examples, system 10 may include a plurality of pacemakers 100, e.g., to deliver electrical stimulation therapy at multiple sites of heart 26 such as within multiple heart chambers for multi-chamber pacing therapies.

Pacemaker 100 is capable of producing electrical stimulation pulses delivered to heart 26 via one or more electrodes on the outer housing of pacemaker 100. Pacemaker 100 includes an acoustic receiver for receiving an acoustical trigger signal emitted by emitting device 18. In response to receiving an acoustical trigger signal, pacemaker 100 delivers one or more pacing pulses.

In one embodiment, pacemaker 100 includes a pulse generator configured to deliver one or more pacing pulses upon receiving an acoustical trigger signal from emitting device 18. Cardiac signal sensing is performed by ICD 14. ICD 14 senses ECG signals through lead 16 and controls pacing delivered by pacemaker 100 via acoustical trigger signals emitted by emitting device 18 under the control of ICD 14.

Intracardiac pacemaker 100 may or may not be configured to sense cardiac signals. Pacemaker 100 may rely solely on a trigger signal from emitting device 18 for controlling the timing of pacing pulse delivery without sensing any other cardiac electrical event signals or any other physiological signals. In order to minimize the size of pacemaker 100, some functions such as cardiac signal sensing and radio frequency telemetry functions may be omitted such that pacemaker 100 includes a pulse generator with limited memory, processing, and other functions directed to therapy delivery.

In other embodiments, pacemaker 100 senses EGM signals in the heart chamber in which it is implanted. Since pacemaker 100 is positioned wholly within a heart chamber, however, the EGM signal sensed by pacemaker 100 will be less sensitive or insensitive to P-waves and/or R-waves occurring in other heart chambers. In past practice, a subcutaneous pacemaker might be coupled to one or more leads that position sense electrodes in or along multiple heart chambers such that multiple sensing channels can be monitored. By monitoring multiple sensing channels, coordinated pacing pulses can be delivered to one or more heart chambers at specified time intervals, e.g., AV or VV intervals.

Since pacemaker 100 may have no or limited sensing capabilities, pacemaker 100 may be "blinded" to intrinsic events, such as intrinsic R-waves, occurring in the same heart chamber and to paced or intrinsic events occurring in other heart chambers. Delivery of CRT, dual chamber pacing, or other multi-chamber pacing therapies may require delivering a pacing pulse at a predetermined time interval after an event, sensed or paced, in another heart chamber. As such, emitting device 18 provides a trigger signal to pacemaker 100 in response to ECG signals sensed by ICD 14 to cause pacing pulses to be delivered by pacemaker 100 at desired time intervals relative to other heart chamber events. Pacemaker 100 (for generating pacing pulses) combined with ICD 14 (for sensing physiological signals and making therapy delivery decisions) provides the functionality required to deliver various therapies that may require synchronization or coordination with cardiac events occurring in the same or a different heart chamber without physical connection between pacemaker 100 and ICD 14 implanted at separate implant sites.

FIG. 2A further depicts programmer 40 in wireless communication with ICD 14 via communication link 42. In some examples, programmer 40 comprises a handheld computing device, computer workstation, or networked computing device. Programmer 40 includes a user interface that presents information to and receives input from a user. It should be noted that the user may also interact with programmer 40 remotely via a networked computing device.

A user, such as a physician, technician, surgeon, electrophysiologist, other caregiver, or patient, interacts with programmer 40 to communicate with ICD 14. For example, the user may interact with programmer 40 to retrieve physiological or diagnostic information from ICD 14. A user may also interact with programmer 40 to program ICD 14, e.g., select values for operational parameters of the ICD 14, including parameters used to control acoustical trigger signal emitting device 18 for controlling pacemaker 100. A user may use programmer 40 to retrieve information from ICD 14 regarding the rhythm of heart 26, heart rhythm trends over time, or arrhythmic episodes.

As indicated, ICD 14 and programmer 40 communicate via wireless communication. Examples of communication techniques may include low frequency or radiofrequency (RF) telemetry, but other techniques may be used. In some examples, programmer 40 may include a programming head that is placed proximate to the patient's body near the ICD 14 implant site in order to improve the quality or security of communication between ICD 14 and programmer 40.

The embodiment illustrated in FIG. 2A is an example configuration of an IMD system 10 and should not be considered limiting of the techniques described herein. In other embodiments, ICD 14 may be coupled to a transvenous intracardiac lead extending into the right ventricle (RV) for positioning RV sensing and pacing electrodes and a defibrillation coil electrode within the RV. An example of an RV lead that could be adapted to carry an emitting device 18 is generally disclosed in commonly-assigned, U.S. Pat. No. 5,545,186 (Olson, et al.). Emitting device 18 may be positioned more distally than shown on lead 16 such that the emitting device 18 is positioned in the RV, opposite pacemaker 100 in the LV. Emitting device 18 may then be enabled to emit an acoustical trigger signal from the RV to the pacemaker 100 in the LV. It is contemplated that numerous configurations of a lead based emitting device 18 may be conceived and emitting device 18 may be positioned along the lead body 17 at relatively more proximal or more distal locations than shown on lead 16 to position emitting device 18 at a desired location relative to pacemaker 100.

Figure 2B:
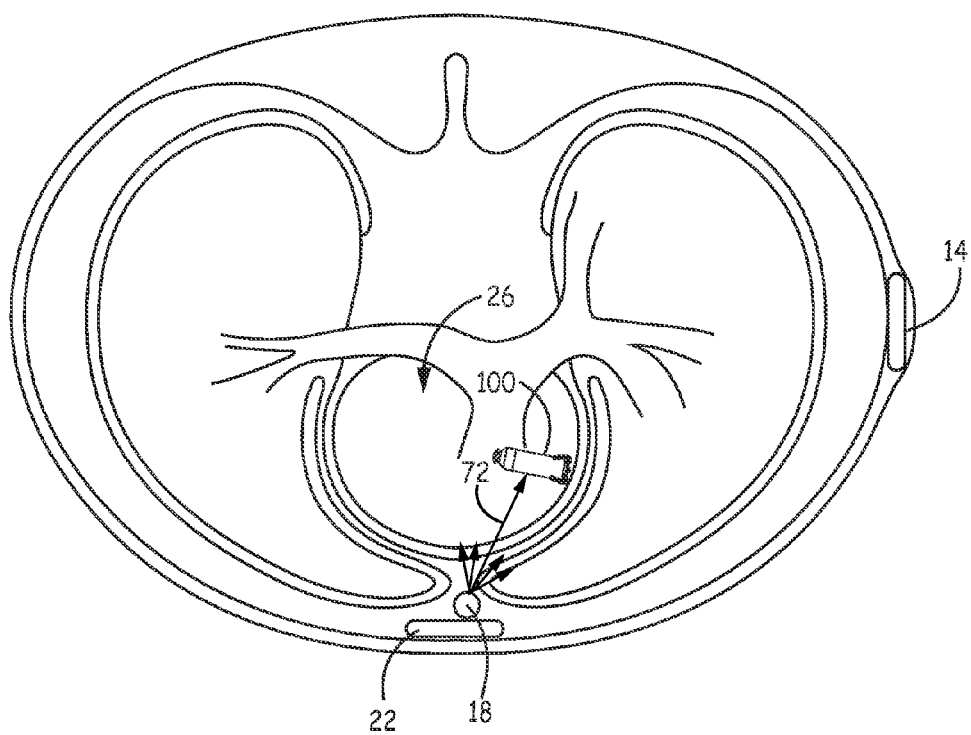
FIG. 2B is a sectional view of the patient's anatomy depicting an alternative configuration of the system of FIG. 2A.

FIG. 2B is a sectional view of the patient's anatomy depicting an alternative configuration of system 10 of FIG. 2A. Emitting device 18 is shown in a substernal position on lead 16 (not seen in the sectional view of FIG. 2B). Instead of being positioned suprasternally, inferior to the xyphoid process, emitting device 18 may be positioned substernally and relatively more superior by advancing the distal end of lead 16 to a substernal location. Emitting device 18 may be configured for directional sound emission with emitting device 18 oriented to generally direct the acoustical signal toward the implant position of pacemaker 100, e.g., along an acoustical path to pacemaker 100 as represented by arrow 72, which may substantially avoid lung tissue.

Lead 16 may be placed under or below the sternum in the mediastinum and, more particularly, in the anterior mediastinum. The anterior mediastinum is bounded laterally by pleurae, posteriorly by pericardium, and anteriorly by sternum. Lead 16 may be at least partially implanted in other extra-pericardial locations, i.e., locations in the region around, but not necessarily in direct contact with, the outer surface of heart 26. These other extra-pericardial locations may include in the mediastinum but offset from sternum 22, in the superior mediastinum, in the middle mediastinum, in the posterior mediastinum, in the sub-xiphoid or inferior xiphoid area, near the apex of the heart, or other location not in direct contact with heart 26 and not subcutaneous. In other embodiments, lead 16 may extend within the pericardium and in direct contact with heart 26. In any of these illustrative implant locations, lead 16 may be positioned to optimally position acoustical emitting device 18 for reliably transmitting a trigger signal to pacemaker 100.

Figure 3A:
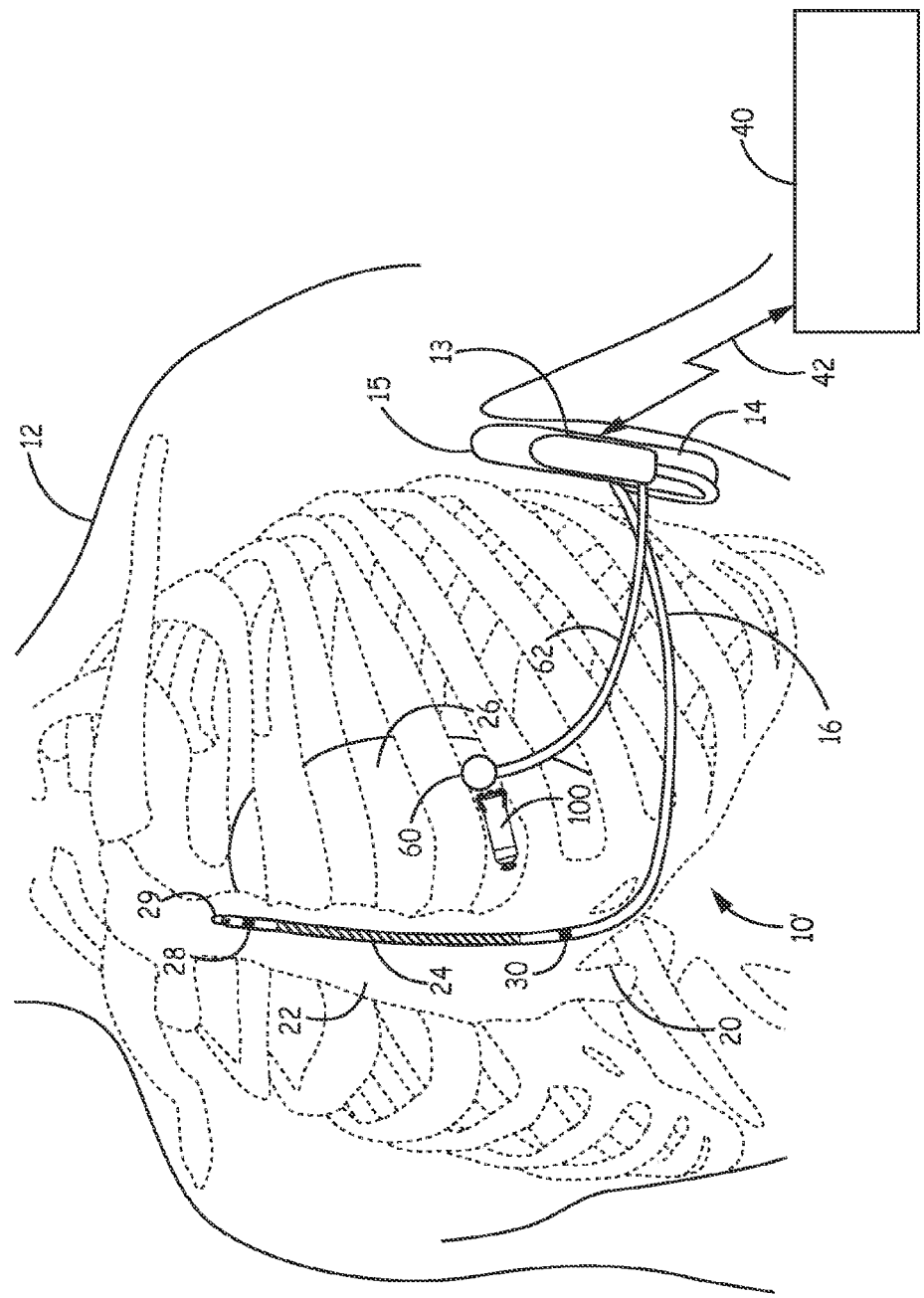
FIG. 3A is a conceptual diagram illustrating an IMD system according to an alternative example.

FIG. 3A is a conceptual diagram illustrating an IMD system 10' according to an alternative example. ICD 14 coupled to lead 16 is used to sense cardiac electrical signals in patient 12 and provide therapy to heart 26 as described above. Intracardiac pacemaker 100 is implanted within the LV and delivers pacing pulses to the LV in response to receiving an acoustical trigger signal. In this embodiment, an acoustical trigger signal emitting device 60 is carried by a separate lead 62 coupled to ICD 14 and positioned extrathoracically, e.g., along an intercostal space, to direct an acoustical trigger signal toward pacemaker 100 through the intercostal space and intervening muscle, blood, myocardial tissue, etc. Emitting device 60 is capable of receiving a control signal from ICD 14 conducted along lead 62. Upon receipt of the control signal, emitting device 60 emits an acoustical trigger signal to cause pacemaker 100 to deliver an LV pacing pulse.

A dedicated lead 60 carrying emitting device 18 may be provided to position emitting device 18 at an optimal location for transmitting a trigger signal to pacemaker 100. An optimal location is a location of emitting device 18 relative to pacemaker 100 that allows a trigger signal to reach pacemaker 100 with adequate signal intensity and signal-to-noise ratio that it is reliably detected by pacemaker 100. A trigger signal path between acoustical emitting device 18 and pacemaker 100 may include tissues that attenuate the trigger signal through absorption or reflection of the signal. The location of emitting device 18 is selected such that acoustical signal losses along the path do not reduce the intensity of the trigger signal below a threshold level that is detectable by pacemaker 100.

Emitting device 60 may have its own battery, which may be rechargeable, such that the power required by ICD 14 for sensing and therapy delivery functions and the power required for acoustical trigger signal emission is distributed across two devices and two (or more) batteries or other power sources.

Emitting device 60 may alternatively be embodied as a leadless device capable of receiving a wireless control signal from ICD 14. Emitting device 60 carried by a dedicated lead 62, or embodied as a leadless emitting device, may be positioned in an optimal location for transmitting an acoustical trigger signal to pacemaker 100 without limitations associated with optimal positioning of electrodes 24, 28 and 30 for sensing ECG signals and delivering shock therapy. A leadless emitting device 60 may be implanted at a desired site without requiring lead tunneling. The emitting device 60 may act as a relay device for transmitting a control signal from ICD 14 to pacemaker 100 by converting an electrically conducted or wirelessly transmitted RF control signal to an acoustical trigger signal that is transmitted to pacemaker 100.

An emitting device 18 or 60 positioned external to the ribcage, such as in or along ICD 14 or positioned subcutaneously along a lead extending from ICD 14, may be positioned such that sound is directed through an intercostal space transmitted through heart 26 or through a rib. Transmission of an acoustical trigger signal along a path through blood and muscle tissue may be more efficient than a path through lung tissue. The frequency of an acoustical trigger signal may be selected to provide efficient transmission through the tissues along the acoustical pathway between an acoustical trigger signal emitting device 18 or 60 and the receiving pacemaker 100.

In some examples, multiple emitting devices may be included in systems 10 or 10'. Depending on the final implant position of pacemaker 100 and shifting that may occur over time, pacemaker 100 may be more sensitive to an acoustical trigger signal emitted by one device than by another device at a different location. Multiple emitting devices positioned at different, spaced apart locations may be selected individually or in combination by ICD 14 to emit an acoustical trigger signal to achieve reliable trigger signal reception by pacemaker 100 using the greatest power efficiency.

Furthermore, it is contemplated that an acoustical emitting device 18 may be located in the ICD 14, e.g., along its housing 15 and/or connector assembly 13. When incorporated along housing 15, the housing thickness, overall or at specified location adjacent the emitting device, e.g., as shown by membrane 9 in FIG. 1B, may be selected such that the housing and the transmitting acoustical transducer of the emitting device resonate together at the operating frequency of the emitting device. In some embodiments, ICD 14 may be implanted relative to pacemaker 100 so that an acoustical signal may be reliably transmitted from ICD 14 to pacemaker 100. The implant location of ICD 14 is selected to establish a defibrillation vector between electrode 24 and ICD housing 15. In other applications, a different type of sensing device may be substituted for ICD 14 that may implanted at a variety of locations that facilitate acoustical signal transmission from the sensing device directly to pacemaker 100 without requiring a lead-based or leadless emitting device spaced apart from the sensing device and pacemaker 100 for relaying the trigger signal.

Figure 3B:
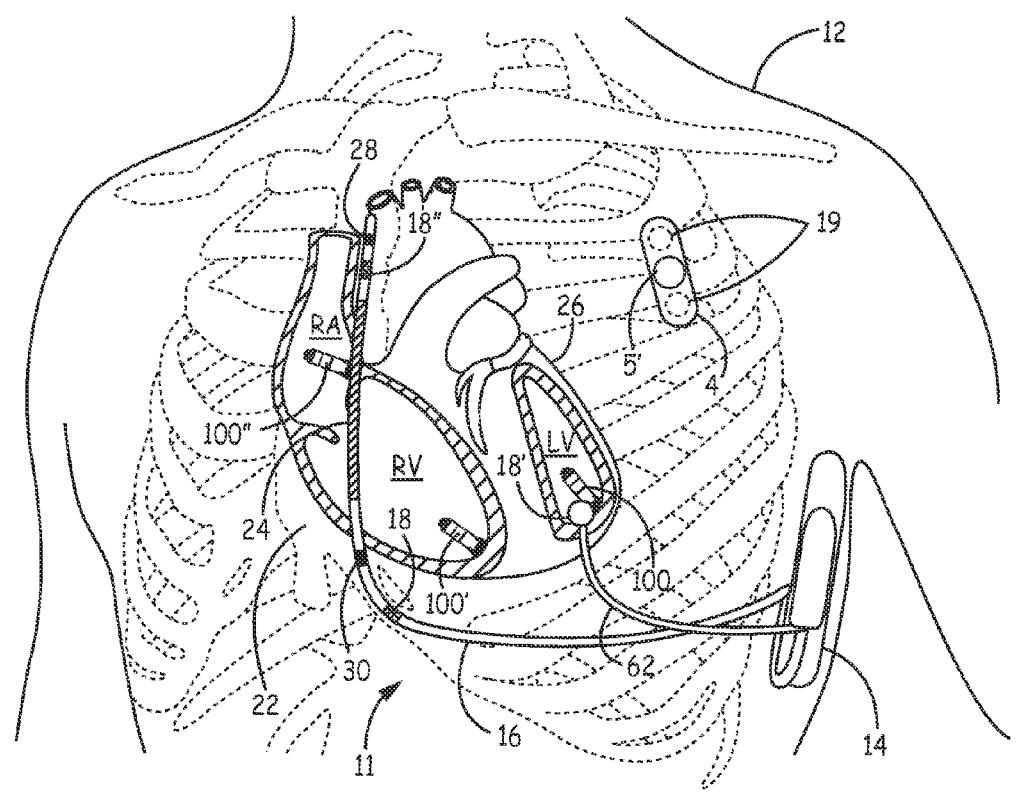
FIG. 3B is a conceptual diagram illustrating an IMD system including multiple therapy delivery devices 100, 100', and 100".

FIG. 3B is a conceptual diagram illustrating an IMD system 11 including multiple therapy delivery devices 100, 100', and 100". In embodiments including multiple intracardiac pacemakers 100, 100' and 100", the acoustic receivers in each pacemaker 100, 100' and 100" may be configured to be sensitive to different signal frequencies. In the example shown, one pacemaker 100 is shown in the LV, pacemaker 100' is shown in the RV and pacemaker 100" is shown in the RA. Emitting device 18 may be controlled (by control signal 95) to emit an acoustical trigger signal at a first frequency for triggering an RV pacemaker 100' configured to detect trigger signals having the first frequency (and ignore other frequencies) and to emit a second acoustical trigger signal at a second frequency for triggering an LV pacemaker 100 configured to detect trigger signals having the second frequency. The emitting device 18 may be controlled by ICD 14 to emit a trigger signal at the first frequency to cause delivery of an acoustically-triggered RV pacing pulse and emit a trigger signal at the second frequency to trigger an LV pacing pulse at a controlled time interval (positive or negative) relative to the triggered pace in the RV. Similarly, RA pacemaker 100" may be triggered to deliver a pacing pulse in response to a third wavelength.

Alternatively, multiple triggered pacemakers 100, 100' and 100" may include acoustic receivers, as described in greater detail below, operating at the same operating frequency but configured to detect different trigger signal patterns that are mutually exclusive. For example, each triggered pacemaker 100, 100' and 100" may be configured to detect an exclusive trigger signal, which may include multiple pulses at predefined pulse intervals, pulse amplitudes and/or other pulse shaping parameters or patterns. An individual triggered pacemaker 100 may be addressed by a specified trigger signal pattern while another triggered pacemaker 100' is addressed by a different trigger signal pattern. Different trigger signal parameters may be used to transmit mutually exclusive trigger signals that are recognized and detected by the appropriate therapy delivery device 100, 100' or 100". Mutually exclusive trigger signal patterns may be defined by different pulse numbers, different interpulse intervals, different pulse widths, different rising and/or falling slope of a trigger signal pulse or any combination thereof.

To illustrate, one therapy delivery device 100 may detect a trigger signal having more than two pulses as invalid while another therapy delivery device 100" may require detection of a minimum of three pulses to recognize a valid trigger signal. In another example, one therapy delivery device 100 may detect a valid trigger signal having a short-long-short interpulse interval pattern and another therapy delivery device 100''' may detect a valid trigger signal as one having a long-short-long interpulse interval pattern.

Alternatively, when two (or more) therapy delivery devices 100 and 100' are included in the IMD system 11, multiple emitting devices 18, 18' and 18", each configured to target a trigger signal at one specific therapy device 100, 100' and 100''' respectively, may be used. For example, paired emitting and therapy delivery devices, 18 paired with 100'; 18' paired with 100 and 18" paired with 100", may be implanted relative to each other so that each emitting device 18, 18''' and 18" is positioned and controlled to focus the emitted trigger signal at a respective therapy delivery device 100',100 and 100'''.

Each of emitting devices 18, 18" and 18''' is shown carried by leads 16 or 62 coupled to ICD 14 but in some examples an emitting device 5' included in an IMD system 11 may be controlled by a sensing-only device 4, which may be provided as an ECG monitor as described in conjunction with FIG. 1A. Emitting device 5' may be one of multiple emitting devices used to control multiple therapy delivery devices 100, 100' and 100" or a single emitting device of IMD system 11 used to control the multiple therapy delivery devices 100, 100' and 100".

Trigger signals may be sequentially steered or focused toward different targeted therapy delivery devices 100, 100' and 100". For example, an array of acoustic transducers included in emitting device 18 or emitting device 5 may be controlled to focus one trigger signal at one therapy delivery device 100 and controlled to focus another trigger signal at another therapy delivery device 100' or 100".

The multiple therapy delivery devices 100, 100' and 100", emitting devices 18, 18' and 18" and sensing devices 4 and 14 shown in FIG. 3B are depicted to illustrate various possible combinations of one or more sensing device, one or more emitting device and/or one or more therapy delivery device that could be included in an IMD system 11 that controls at least one triggered therapy delivery device using an acoustical trigger signal. Any variation or combination of these devices may be used to deliver a therapy triggered by an acoustical trigger signal. A therapy delivery system employing the techniques disclosed herein may include different combinations and arrangements of at least one therapy delivery device, at least one sensing device and at least one trigger signal emitting device than the combinations and arrangements shown in the accompanying drawings.

Figure 4:
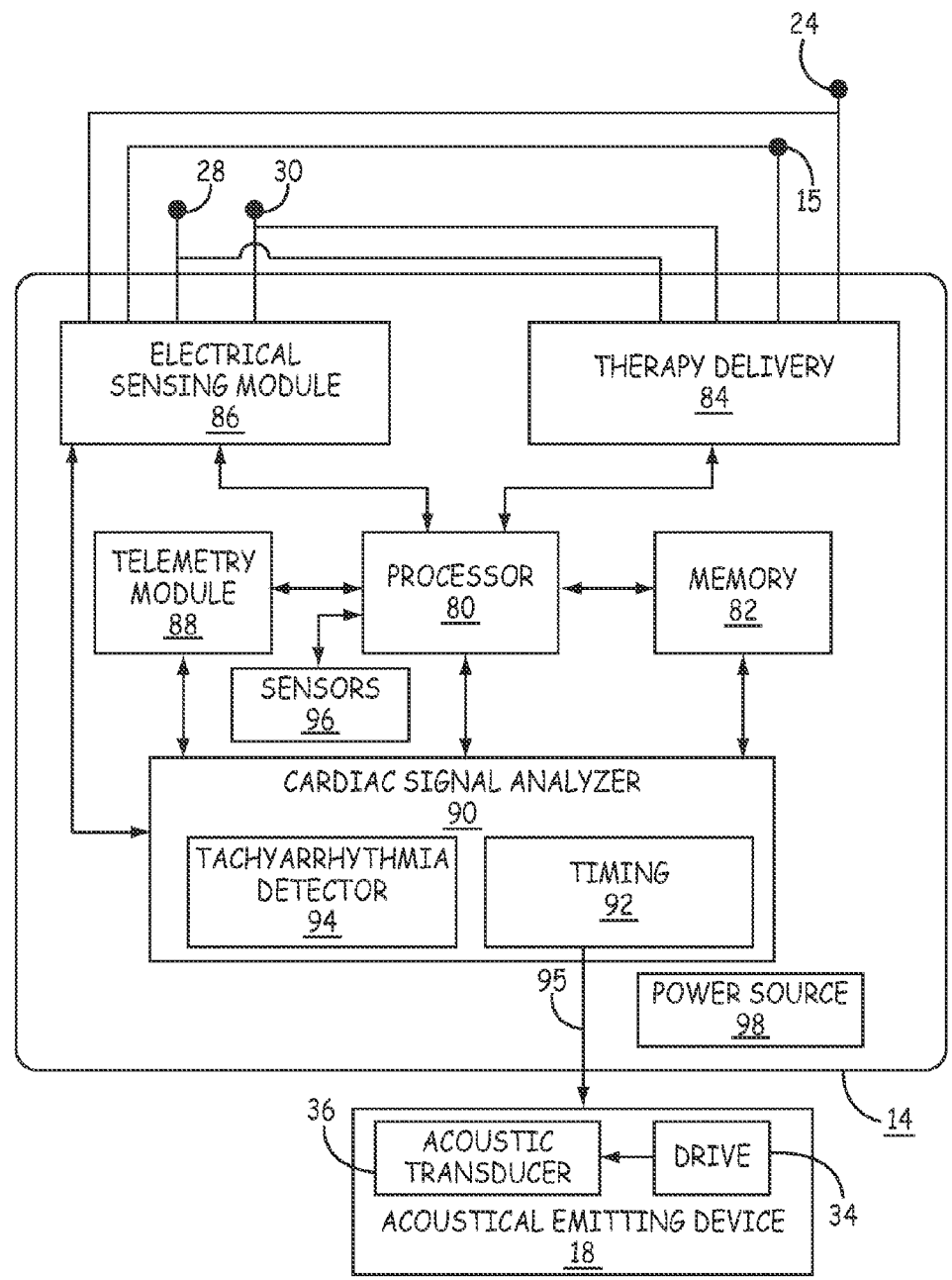
FIG. 4 is a functional block diagram of electronic circuitry that is included in one embodiment of the ICD shown in FIGS. 2A and 3.

FIG. 4 is a functional block diagram of electronic circuitry that is included in one embodiment of ICD 14 shown in FIGS. 2A and 3. The ICD 14 includes electrical sensing module 86, therapy delivery module 84, telemetry module 88, processing and control module 80, also referred to herein as "control module" 80, memory 82, and cardiac signal analyzer 90. A power source 98 provides power to the circuitry of ICD 14, including each of the modules 80, 82, 84, 86, 88, 90. Power source 98 may include one or more energy storage devices, such as one or more rechargeable or non-rechargeable batteries.

The functional blocks shown in FIG. 4 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 and/or pacemaker 100 may be implemented in a processing and control module 80 executing instructions stored in memory 82.

Processing and control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16, e.g., as shown in FIG. 2A, and housing 15, at least a portion of which also serves as a common or ground electrode.

Electrical sensing module 86 is coupled to electrodes 28 and 30 in order to monitor electrical activity of the patient's heart. Electrical sensing module 86 may optionally be coupled to electrodes 24 and 15 and enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers included in sensing module 86. Switching circuitry may include a switch array, switch matrix, multiplexer, or any other type of switching device suitable to selectively couple sense amplifiers to selected electrodes. A sensing vector between electrodes 28 and 30 may be selected for sensing an ECG signal or sensing vector may be selected that utilizes coil electrode 24 and/or housing 15, e.g., from sensing electrode 28 to housing 15 or from sensing electrode 30 to housing 15.

One or more ECG signals are received by an input of sensing module 86. Sensing module 86 includes one or more sense amplifiers or other cardiac event detection circuitry for sensing cardiac events, e.g., P-wave and/or R-waves, from the ECG signal(s). Sensing module 86 includes sense amplifiers that pass sense event signals to cardiac signal analyzer 90. For example P-wave sense signals and R-wave sense signals are passed to cardiac signal analyzer 90 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 92. In response to the pacing escape interval expiring, a control signal 95 is passed to the acoustical signal emitting device 18. The pacing escape interval is restarted upon a trigger signal or a sense event signal. Other pacing intervals, such AV or VV pacing intervals are started by control module 80 upon sensing an event in one cardiac chamber, atrial or ventricular, and sending a trigger signal to pacemaker 100 to deliver a pacing pulse synchronized to the sensed event at the AV or VV interval.

The control signal 95 in the illustrative examples presented herein may be referred to as a pacing control signal because it causes pacemaker 100 to deliver a pacing pulse to a heart chamber. In other examples, the control signal 95 may be produced by cardiac signal analyzer 90 to cause other types of therapy pulses to be delivered by pacemaker 100 (or another therapy delivery device). For example control signal 95 may be produced to cause pacemaker 100 or another therapy delivery device to deliver an ATP pulse, a vagal nerve stimulation pulse, or other type of electrical stimulation pulse.

The control signal 95 is an electrical signal that is passed to emitting device 18 along lead 16 (or another lead carrying emitting device 18) when emitting device is coupled to ICD 14 in a wired connection. The control signal 95 is alternatively an electrical signal that is passed to telemetry module 88 where it is converted to a wireless telemetry signal that is transmitted via telemetry module 88, to emitting device 18. Emitting device 18 may be carried by a lead but configured to wirelessly receive a control signal 95 from telemetry module 88. Alternatively, the emitting device is not a lead-based emitting device and receives a wireless control signal, e.g., an RF signal, from telemetry module 88.

Acoustical signal emitting device 18 includes a drive signal circuit 34 that receives the control signal 95, either as a wired electrical signal or a wireless signal from telemetry module 88. Drive signal circuit 34 enables an acoustic transducer 36 to emit an acoustical trigger signal. As described herein, the acoustical trigger signal is received and detected by pacemaker 100 to cause pacemaker 100 to deliver one or more pacing pulses to the patient's heart. The acoustical trigger signal may be generated according to pre-set frequency, amplitude, duration and other signal characteristics. In other words, the control signal may only signal the emitting device 18 that a trigger signal is needed. The trigger signal merely signals pacemaker 100 to delivery therapy without signaling any information relating to how many pacing pulses, what pulse amplitude or pulse width or other pacing pulse control parameter information. Pacemaker 100 may be programmed to deliver a predetermined number of pacing pulses according to predefined pulse control parameters when the trigger signal is detected.

Alternatively, control signal 95 may include encoded pacing pulse control information. The control signal generated by drive signal circuit 34 may cause transducer 36 to emit a trigger signal according to a frequency, duration, amplitude or other characteristic of the trigger signal that is intentionally adjusted according to the control signal. The control signal 95 signals the emitting device 18 that a trigger signal is needed as well as what characteristic(s) the emitted trigger signal should have. Pacemaker 100 may be configured to detect the characteristic(s) of the emitted trigger signal and set a pacing pulse control parameter based on that characteristic.

Transducer 36 may be embodied as one or more ultrasonic transducers configured to emit sound upon receiving a drive signal from circuit 34. For example, transducer 36 may include one or more microelectromechanical systems (MEMS) device, ceramic piezoelectric crystals, polymer piezoelectric crystals, capacitive micromachined ultrasonic transducers (CMUT), or other ultrasonic transducers. Transducer 36 may include multiple transducers arranged in an array and/or configured to emit acoustical signals in multiple directions from emitting device 18 to promote reception of the acoustical trigger signal by pacemaker 100 despite shifting, rotation or other changes in the relative orientations of emitting device 18 and pacemaker 100 with respect to each other. The multiple transducers may be selectable by drive signal circuit 34 such that a single one or combination of transducers producing the best signal-to-noise ratio at the pacemaker receiver is selected.

Transducer 36 may include multiple transducers activated by drive signal circuit 34 to emit sound waves that constructively interfere to improve the efficiency of acoustical signal transmission. In embodiments that include more than one emitting device, such as one or more lead-based emitting devices, one or more leadless emitting devices, and/or one or more emitting devices incorporated in ICD 14, two or more emitting devices may be activated synchronously to produce ultrasound waves that superimpose at the receiver of pacemaker 100 to increase transmission efficiency and/or improve signal reception. A phased array of transducers that can be independently pulsed to emit sound can be used to focus the acoustical signal toward the intended receiver. When multiple pacemakers 100 or other therapy delivery devices are included, a phased array of transducers included in transducer 36 may be controlled by drive signal circuit 34 to pulse the transducers in a programmed time relationship to focus the acoustical trigger signal on the receiver of an intended therapy delivery device.

Transducer 36 may include different types of transducers configured to emit different sound frequencies. The different transducers are selectable by drive signal circuit 34 to enable transmission of different frequencies of acoustical trigger signals. For example, different frequencies or different patterns of amplitude, frequency, pulse number, etc. may be emitted for triggering different responses by pacemaker 100 or for triggering different intracardiac pacemakers when multiple pacemakers are implanted. For example, different acoustical trigger signals may be used to cause pacemaker 100 to deliver one or more pacing pulses defined by different pulse shape, pulse amplitude, pulse width, pulse frequency or other stimulation pulse parameter.

The transducer 36 is configured to emit sound at an amplitude and frequency that is detectable by the pacemaker receiver after attenuation by body tissues along the pathway between the transducer 36 and the pacemaker receiver. In one example, transducer 36 is configured to emit sounds in the range of approximately 40 kHz to over 1 MHz. The frequency of the trigger signal is selected in part based on the expected types of body tissues encountered along the acoustical pathway for a particular medical application.

Timing circuit 92 may generate a control signal 95 to trigger pacemaker 100 to deliver pacing pulses to provide bradycardia pacing, atrial-synchronized ventricular pacing, ATP, cardiac resynchronization therapy, AV nodal stimulation, or other pacing therapies according to pacing algorithms and timing intervals stored in memory 82. Bradycardia pacing may be delivered temporarily to maintain cardiac output after delivery of a cardioversion-defibrillation shock by ICD 14 as the heart recovers back to normal function post-shock.

Cardiac signal analyzer 90 includes a tachyarrhythmia detector 94 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 (Greenhut, et al.), hereby incorporated herein by reference in its entirety. The timing of R-wave sense signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized ECG signals to cardiac signal analyzer 90 for use in detecting tachyarrhythmia. Examples of ICDs that may be adapted for use with a triggered pacemaker 100 and operations that may be performed by tachyarrhythmia detector 94 for detecting and discriminating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316 (Gillberg et al.), U.S. Pat. No. 5,545,186 (Olson, et al.), and U.S. Pat. No. 5,855,593 (Olson, et al.), all of which patents are incorporated herein by reference in their entirety.

The detection algorithms are highly sensitive and specific for the presence or absence of life threatening VT and VF. Therapy delivery module 84 includes a HV therapy delivery module including one or more HV output capacitors. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using coil electrode 24 and housing 15.

It should be noted that implemented tachyarrhythmia detection algorithms may utilize not only ECG signal analysis methods but may also utilize supplemental sensors 96, such as tissue color, tissue oxygenation, respiration, patient activity, heart sounds, and the like, for contributing to a decision by processing and control module 80 to apply or withhold a defibrillation therapy. Sensors 96 may also be used in determining the need for pacing and timing of pacing pulses by pacemaker 100. For example, an activity sensor signal or other rate responsive signal, such as a minute ventilation signal, may be used for determining a pacing rate meeting a patient's metabolic demand. Timing circuit 92 produces a control signal 95 to cause emitting device 18 to generate acoustical trigger signals that cause pacemaker 100 to deliver pacing pulses at an appropriate rate based on the rate responsive signal. Sensors 96 may include one or more sensors carried by a lead extending from ICD 14, within or along housing 15, and/or connector block 13.

Telemetry module 88 includes a transceiver and antenna for communicating with another device, such as an external programmer 40 and emitting device 18 when it is configured to receive wireless control signals 95. Under the control of control module 80, telemetry module 88 may receive downlink telemetry from and send uplink telemetry to programmer 40 or other external device. Telemetry module 88 may transmit control signal 95 wirelessly to emitting device 18, e.g., as an RF signal.

Figure 5:
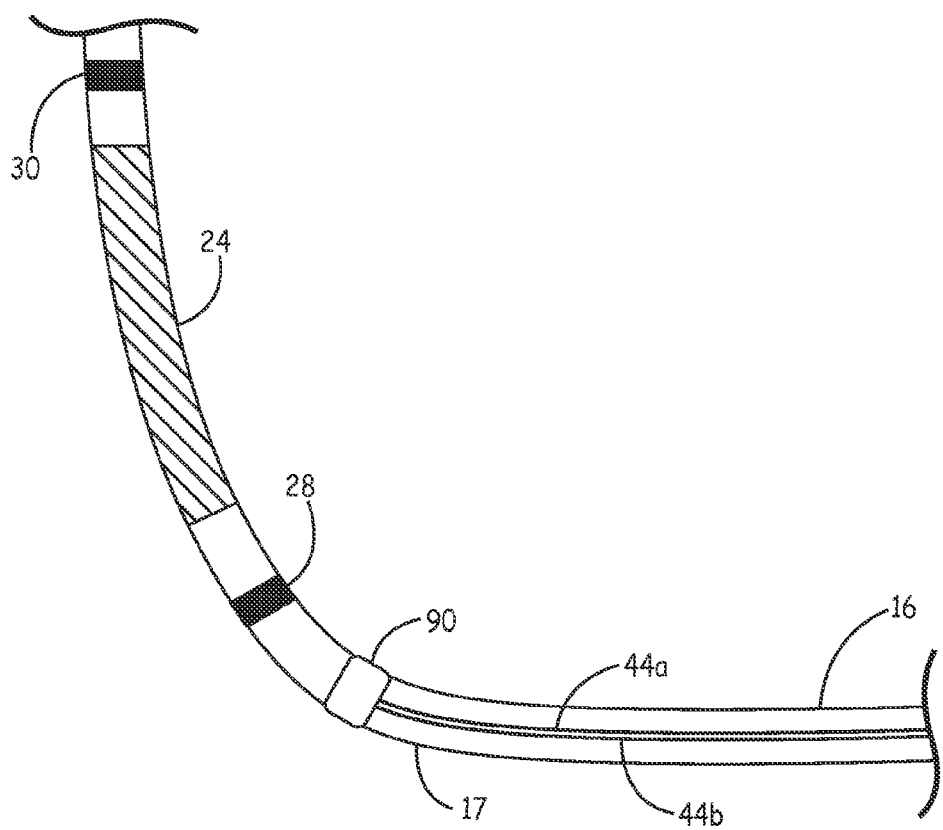
FIG. 5 is a partial view of the defibrillation and sensing lead shown in FIG. 2A according to one embodiment.

FIG. 5 is a partial view of lead 16 according to one embodiment. Emitting device 18 shown in FIG. 2A may include a torus ultrasound transducer 90 for emitting acoustic signals. Transducer 90 may be fitted circumferentially around the elongated, insulative lead body 17 of lead 16. In this case, an inner diameter of transducer 90 may be approximately equal to an outer diameter of lead body 17. Alternatively, transducer 90 may be exposed through an opening in lead body 17. The maximum outer diameter of torus transducer 90 may be approximately equal to the outer diameter of lead body 17. In other examples, the maximum outer diameter of torus transducer 90 may be greater than the outer diameter of lead body 17, and the inner diameter of torus transducer 90 is less than the outer diameter of lead body 17. For example, transducer 90 may be coupled between ends of segments of lead body 17, which may include the use of additional coupling members, e.g., rings or annular connectors, to assemble transducer 90 along lead body 17. While a torus transducer is shown, it is recognized that other shapes or types of transducers may be carried by lead body 17.

Transducer 90 is coupled to a pair of conductors 44a and 44b, collectively 44, extending through elongated lead body 17 to a proximal connector for electrical connection to ICD circuitry. Other conductors extending through lead body 17 to electrodes 24, 28 and 30 are not shown in FIG. 5 but it is understood that respective insulated conductors would be carried by lead body 17 to respective electrodes.

Conductors 44 extend from transducer 90 to drive signal circuit 34 (FIG. 4). Transducer 90 is activated by a drive signal conducted from drive signal circuit 34 to transducer 90 via conductors 44. Upon activation, transducer 90 generates an acoustical trigger signal. Since transducer 90 is not used for sensing acoustic signals, additional conductors or switches for conducting signals from transducer 90 to a sensing circuit are not required. In this example, the conductors 44 extending from transducer 90 are coupled only to the drive signal circuit 34 (which may include a ground connection to housing 15) for carrying an ICD-generated control signal to transducer 90 that causes acoustic signal emission by transducer 90.

Figure 6A:
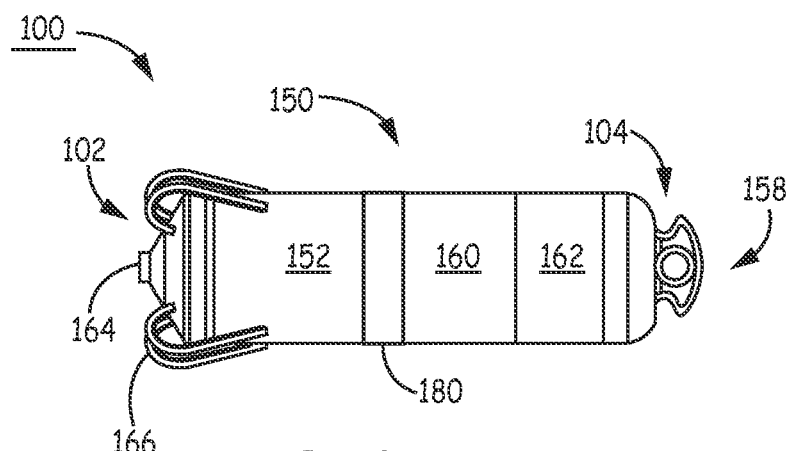
FIG. 6A is a conceptual diagram of the triggered pacemaker included in the IMD systems of FIGS. 2A and 3.

FIG. 6A is a conceptual diagram of triggered pacemaker 100. Pacemaker 100 includes electrodes 162 and 164 spaced apart along the housing 150 of pacemaker 100. Electrode 164 is shown as a tip electrode extending from a distal end 102 of pacemaker 100, and electrode 162 is shown as a ring electrode along a mid-portion of housing 150, for example adjacent proximal end 104. In alternative embodiments, pacemaker 100 may include two or more ring electrodes or other types of electrodes exposed along pacemaker housing 150 for delivering electrical stimulation to heart 26. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

The housing 150 includes a control electronics subassembly 152, which houses the electronics for producing stimulation pulses and performing therapy delivery functions of pacemaker 100. As one example, control electronics subassembly 152 may include a pulse generator and an acoustic receiver for receiving the acoustical trigger signal from emitting device 18 and triggering the pulse generator to deliver a pacing pulse via electrodes 162 and 164 in response to the acoustical trigger signal.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which patents are incorporated herein by reference in their entirety. Housing 150 is formed from a biocompatible material, such as stainless steel, titanium or alloy thereof. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150. Electrodes 162 and 164 form an anode and cathode pair for bipolar cardiac pacing. In some embodiments, electrodes 162 and 164 are also used for sensing cardiac EGM signals, in which case control electronics subassembly 152 includes sensing circuitry.

Pacemaker 100 may include a set of active fixation tines 166 to secure pacemaker 100 to patient tissue, e.g., by interacting with the ventricular trabeculae. Pacemaker 100 may include a set of active fixation tines as disclosed in commonly-assigned, pre-grant publication U.S. 2012/0172892 (Grubac, et al.), hereby incorporated herein by reference in its entirety. Fixation tines 166 are configured to anchor pacemaker 100 to position electrode 164 in operative proximity to a targeted tissue for delivering electrical stimulation pulses. Numerous types of active and/or passive fixation members may be employed for anchoring or stabilizing pacemaker 100 in an implant position.

Pacemaker 100 may further include a delivery tool interface 158. Delivery tool interface 158 is located at the proximal end of pacemaker 100 and is configured to connect to a delivery device, such as a catheter, used to position pacemaker 100 at an implant location during an implantation procedure, for example within a heart chamber.

Pacemaker 100 includes an acoustic coupling member 180 for coupling an acoustical trigger signal from emitting device 18 to a receiving transducer enclosed within housing 150. An acoustic transducer included in control electronics subassembly 152 receives vibrations incident on coupling member 180 and produces an electrical signal that is compared to a trigger detection threshold. When a trigger signal is detected, pacemaker 100 delivers at least one pacing pulse.

When pacemaker 100 is advanced transvenously into a heart chamber, the final orientation of pacemaker 100 may vary and the final orientation of coupling member 180 relative to the patient's anatomy, and therefore relative to emitting device 18 may be unknown. Furthermore, the orientation of coupling member 180 relative to the emitting device 18 may fluctuate over time due to shifting of either pacemaker 100 or emitting device 18 or due to cardiac motion, respiratory motion, or other body motion. As such, coupling member 180 may be a continuous member circumscribing housing 150 to receive ultrasonic vibrations from all sides of pacemaker 100. As described below, coupling member 180 may be machined to have one or more flat surfaces that couple vibrations to one or more transducers mounted on an interior surface of member 180. In other embodiments coupling member 180 may be discontinuous and include multiple segmented members along the circumference of housing 150 for receiving trigger signals from multiple directions. It is contemplated that numerous configurations for one or more coupling members along distal end 102, proximal end 104 or along the outer circumference of housing 150 may be conceived.

Coupling member 180 may be formed of materials that include, without limitation, a metal, such as titanium, stainless steel, gold, platinum, or alloys thereof, glass, ceramic, sapphire, silicon or other material. The thickness of coupling member 180 is selected in consideration of the receiving acoustic transducer thickness such that the combination of the coupling member and the transducer resonate together at a targeted operating frequency. To illustrate, in one embodiment the thickness of a titanium coupling member 180 may be approximately 0.2 mm for a 1 MHz operating frequency, and the piezoelectric transducer material thickness may be adjusted according to the thickness of coupling member 180 as needed. In some examples, with no limitation intended, coupling member 180 may be approximately 0.01 to 0.5 mm in thickness as measured along the flat surfaces of coupling member 180 (e.g., flat facet 308 FIG. 7B).

Figure 6B:
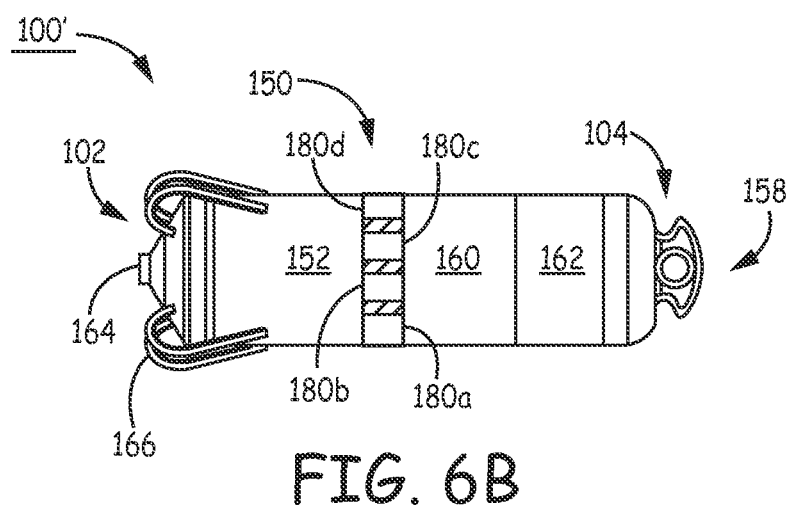
FIG. 6B is a conceptual diagram of a triggered pacemaker according to an alternative embodiment.

FIG. 6B is a conceptual diagram of pacemaker 100 according to an alternative embodiment. Instead of a continuous acoustic coupling member 180 as shown in FIG. 6A, multiple discrete coupling members 180a through 180d may be distributed along multiple sides of pacemaker 100. Pacemaker 100 is shown having a generally cylindrical housing 150 in FIGS. 6A and 6B. In other embodiments, pacemaker 100 may have a prismatic housing including multiple coupling members or a continuous coupling member extending along one or more sides of the housing.

An acoustic transducer may be positioned along an inner surface of each of the coupling members 180a through 180d. When multiple receiving transducers are included, a single transducer producing the greatest voltage signal due to incident vibrations may be selected through switching circuitry for use in detecting trigger signals. Alternatively a combination of transducers may be used in a logical OR or AND operation for the detection of the acoustical trigger signal. For example the voltage signals produced by multiple receiving transducers may be summed and compared to a trigger detection threshold.

Figures 7A, 7B, 7C:
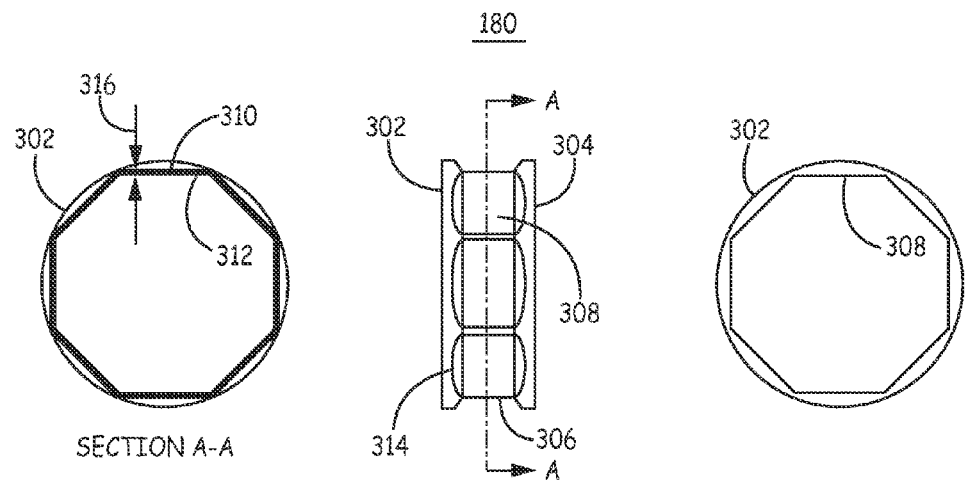
FIGS. 7A, 7B and 7C are sectional, side and end views, respectively, of one example configuration for an acoustic coupling member included in the pacemaker shown in FIG. 6A.

FIGS. 7A, 7B, and 7C are sectional, side and end views of one example configuration for coupling member 180 in pacemaker 100. Coupling member 180 is generally tubular including cylindrical opposing ends 302 and 304 separated by a side wall 306 having multiple facets 308. A generally cylindrical shape of pacemaker housing 150 may facilitate delivery of pacemaker 100 to a target therapy delivery site with the use of a delivery tool such as a catheter. The cylindrical shape may also promote patient comfort and fit at an implant site. The outer cylindrical surface, however, is less efficient in coupling acoustic signals to a piezoelectric transducer within pacemaker 100. To minimize attenuation of the acoustic signal by the pacemaker housing, a coupling member 180 is incorporated along housing 150 as shown in FIG. 6A having flat facets 308 of uniform thickness to provide efficient acoustical coupling of an acoustical trigger signal to piezoelectric elements mounted to an interior surface 312 of each facet 308.

Side wall 306 includes transition portions 314 which are sloped or beveled portions between round cylindrical ends 302 and 304 and facets 308. As seen in the sectional view of FIG. 7A and the end view of FIG. 7C, the ends 302 and 304 have a circular cross-section and the side wall 306 may be polygonal in cross-section depending on the number of facets 308 formed along the side wall 306. For example six facets may be provided along a generally hexagonal side wall 306; eight facets may be provided along a generally octagonal side wall 306, etc. The number of facets may vary between embodiments and will depend on pacemaker size, number of piezoelectric elements desired, size of piezoelectric elements and other factors. In order to provide uniform signal sensitivity from multiple directions or substantially 360 degrees around pacemaker 100, facets 308 may be equally distributed along the circumference of coupling member 308 such that piezoelectric transducers can be mounted along the respective inner surfaces 312 to receive signals coming from any direction.

The coupling member 180 may be a molded and/or machined component formed from any of the example materials listed above. Each facet 308 includes a planar inner surface 312 parallel to a planar outer surface 310 separated by a facet thickness 316. Facet thickness 316 is selected in consideration of the thickness of the piezoelectric transducer coupled to inner surface 312 so that the facet 316 and the transducer resonate together at a desired operating frequency. As can be seen in FIGS. 7A, 7B and 7C, coupling member 108 will have varying thicknesses, but along facets 308 thickness 316 is uniform and may be in the range of 0.03 mm to 0.5 mm depending on the operating frequency of emitted trigger signals and the material thickness of the piezoelectric transducer, which may be adjusted according to thickness 316 of facets 308.

The round cylindrical ends 302 and 304 are configured to mate with adjacent housing portions, e.g., control electronics subassembly 152, battery subassembly 160, a fixation member and tip electrode assembly, and/or electrode 162. Ends 302 and 304 are sealed to adjacent housing portions, for example, without limitation, by welding, brazing, fusion bonding, or adhesive bonding. Ends 302 and 304 may include a mating male, female or threaded feature for interfacing with adjacent housing portions. Rounded cylindrical ends 302 and 304 provide exact mating (within specification tolerances) with adjacent cylindrical subassemblies and thereby facilitate assembly of the coupling member 180 and associated piezoelectric transducers with the control electronics subassembly 152, battery subassembly 160, and electrode 162. In such constructions, it is understood that intervening ferrules, connector rings, or other members may be utilized to assemble acoustic coupling member 180 with the adjacent components of housing 150 and/or electrode 162. In other examples, the opposing ends 302 and 304 of a generally tubular coupling member may have a different geometry, such as a polygonal geometry, configured to mate with a matching geometry of a housing subassembly.

Figures 8A, 8B, 8C:
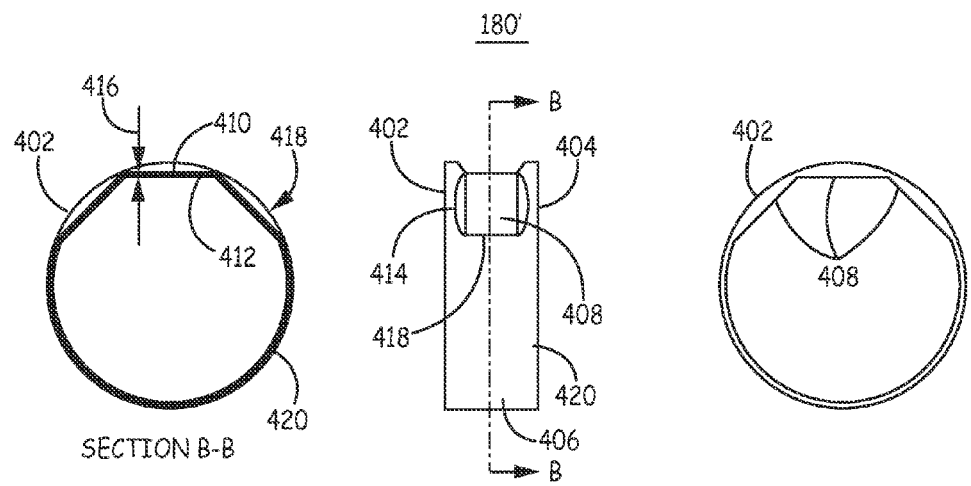
FIGS. 8A, 8B, and 8C are sectional, side and end views, respectively, of an alternative embodiment of an acoustic coupling member.

FIGS. 8A, 8B, and 8C are sectional, side and end views, respectively, of an alternative embodiment of a coupling member 180'. In other examples, coupling member 180' is configured to receive acoustic signals from a known direction. Instead of distributing facets for attaching piezoelectric elements at evenly spaced intervals along the entire circumference of the coupling member, as shown in FIG. 7A, the coupling member 180' may have facets that are distributed at uneven intervals along the circumference of the coupling member 180' or at even intervals along an arc of the circumference of the coupling member 180' that is less than the entire circumference.

For example, coupling member 180' is shown in FIGS. 8A-8C to include a side wall 406 extending between opposing ends 402 and 404. Side wall 406 has a faceted portion 418 and a non-faceted portion 420. Faceted portion 418 is shown to include three equally-sized adjacent facets 408. Each facet 408 is defined by an inner planar surface 412 and an outer planar surface 410 separated by a uniform facet thickness 416. A beveled transition portion 414 extends between each facet 408 and each of the opposing cylindrical ends 402 and 404. As described above, the facet thickness 416 is selected such that the facets 408 and a piezoelectric transducer that is coupled to the inner surface 412 resonate together at a desired operating frequency in response to an acoustical trigger signal. The non-faceted portion 420 may have a round, cylindrical outer and inner surface that matches the round cylindrical ends 402 and 404 and may have the same or different thickness than facets 408.

In other examples, side wall 406 may include a single facet, two opposing facets positioned in 180 degree opposition from each other, four facets equally spaced at 90 degrees from each other, or any other number or spacing of facets along the side wall 406. Any non-faceted portions of side wall 406 may be rounded and may define a constant outer diameter with ends 402 and 404. Ends 402 and 404 retain a round, cylindrical geometry along both the faceted and non-faceted portions 418 and 420 of side wall 406 to facilitate mating and sealing with other housing subassemblies.

Figure 9:
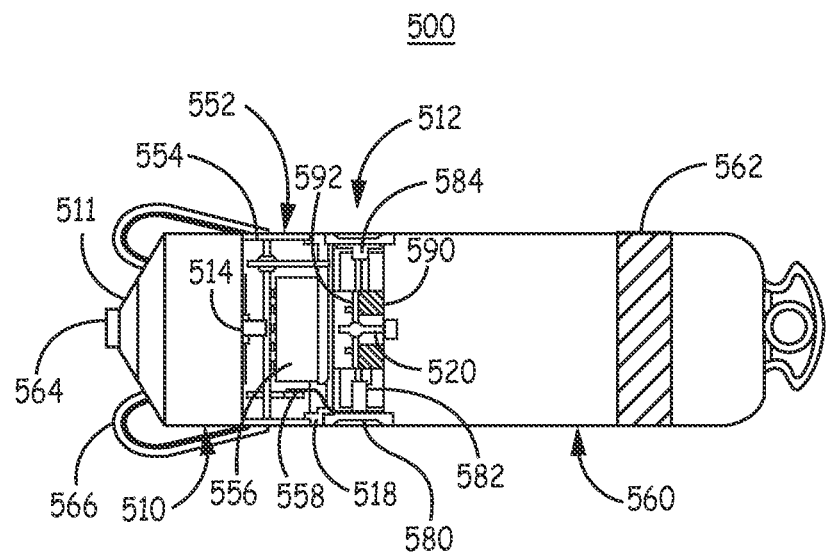
FIG. 9 is a side open view of a triggered pacemaker according to one example.

FIG. 9 is a side open view of a pacemaker 500 according to one example. Pacemaker 500 includes an electrode and fixation member subassembly 510, control electronics subassembly 552, acoustic receiver 512, and battery subassembly 560. The electrode and fixation member subassembly 510 includes tip electrode 564, which may be surrounded by a monolithic controlled release device (MCRD) 511, passive fixation members 566, and electrical feedthrough 514. MCRD 511 may be positioned around electrode 564 for eluting a drug, such as an anti-inflammatory steroid, antibiotic or other pharmacological agent. In one example, MCRD 511 includes sodium dexamethasone phosphate compounded in silicone. Insulated electrical feedthrough 514 extends to control electronics subassembly 552 for electrically coupling electrode 564 to integrated circuit 556.

Control electronics subassembly 552 includes a housing 554 that encloses integrated circuit 556. Integrated circuit 556 controls the various functions of pacemaker 500 (and pacemaker 100) as described herein. Housing 554 of control electronics subassembly 552 is mechanically coupled to a shield member 518, which in turn is mechanically coupled to one end of acoustic coupling member 580. Acoustic coupling member 580 is joined, along its opposing end, to battery subassembly 560. A ring electrode 562 may extend along battery subassembly 560 or another portion of the housing of pacemaker 500, and may be an uninsulated portion of the housing of battery subassembly 560.

Acoustic coupling member 580 may correspond to coupling member 180 shown in FIG. 7A-7C or 180' in FIGS. 8A-8C. An acoustic receiver 512 is enclosed in coupling member 180 and includes multiple piezoelectric transducers 582 and rectifier diodes 584 for producing an electrical signal in response to vibrations imposed on the facets of coupling member 580 by an acoustical trigger signal. A battery feedthrough 520 extends from battery subassembly 560 to a flexible circuit 592, which is electrically coupled to flexible circuit connector 558 that makes electrical connections between integrated circuit 556 and the battery subassembly 560 and acoustic receiver 512.

In the example shown in FIG. 9, a piezoelectric transducer 590 is positioned against battery subassembly 560, e.g., around battery feedthrough 520, and coupled to an associated rectifier diode (not shown in FIG. 9) and flexible circuit 592. The battery subassembly 560 may transmit vibrations caused by the acoustical trigger signal to piezoelectric transducer 590. Piezoelectric transducer 590 is configured to produce an electrical signal in response to vibrations of battery subassembly 560, which can contribute to detecting an acoustical trigger signal by pacemaker 500.

Figure 10:
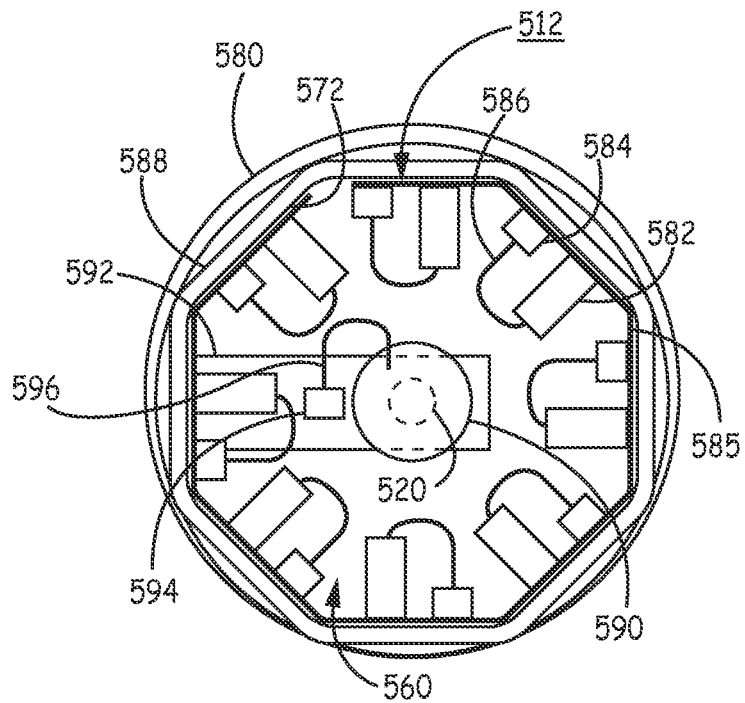
FIG. 10 is a top sectional view of an acoustic coupling member and acoustic receiver included in the pacemaker of FIG. 9.

FIG. 10 is a top sectional view of coupling member 580 and acoustic receiver 512. In this example, acoustic receiver 512 includes a flexible substrate 585 coupled along faceted inner surface 572. A piezoelectric transducer 582 and rectifier diode 584 are coupled to the flexible substrate 585 along each facet 588 of acoustic coupling member 580. The anode of each rectifier diode 584 receives an electrical signal produced by a respective piezoelectric transducer 582 on conductor 586.

Battery feedthrough 520 is coupled to flexible circuit 592 to eliminate a separate additional connection from battery feedthrough 520 to control electronics subassembly 552. Since a flexible circuit 592 is used for transducers 582 and diodes 584 and is connected to control electronics subassembly 592, a conductive trace can be added to flexible circuit 592 for facilitating battery connection to simplify the assembly of pacemaker 500. Piezoelectric element 590, positioned against battery subassembly 560, is coupled to a rectifier diode 594 via conductor 596. Rectifier diode 594 passes a signal to integrated circuit 556 (FIG. 9) via flexible circuit 592 and flexible circuit conductor 558.

The piezoelectric transducers 582 and respective diodes 584 are arranged electrically in parallel between electrical ground and a trigger signal detection circuit included in control electronics subassembly 552. The trigger signal detection circuit (not shown in FIG. 10) may include a digital comparator for receiving the input from the parallel circuit of transducers 582 and diodes 584 and comparing the input to a trigger detection threshold. If the transducer 582 producing the highest voltage signal is greater than the trigger detection threshold, the acoustical trigger signal is detected. In one example, the cathodes of all the rectifier diodes 584 are electrically connected to and drive the gate of a switching field effect transistor (FET). Alternatively, the rectified voltage signals from all diodes 584, 594 may be summed and compared to a trigger detection threshold by integrated circuit 556.

In the octagonal, symmetrical arrangement of acoustic receiver 512 as shown, pacemaker 500 is sensitive to acoustical signals from all directions. In other embodiments, acoustic receiver 512 may be configured in a non-symmetrical arrangement for directional sensitivity, for example using acoustic coupling member 180' shown in FIGS. 8A-8C. It is contemplated that fewer or more piezoelectric transducers 582 and associated rectifier diodes 584 may be included in receiver 512.

In one example, flexible substrate 585 is a flat strip that piezoelectric transducers 582 and diodes 584 are assembled onto. Substrate 585 may be adhesively bonded to the inner surface 572 of acoustic coupling member 580. For example, substrate 585 may be a double-sided flexible circuit tape.

Figure 11:
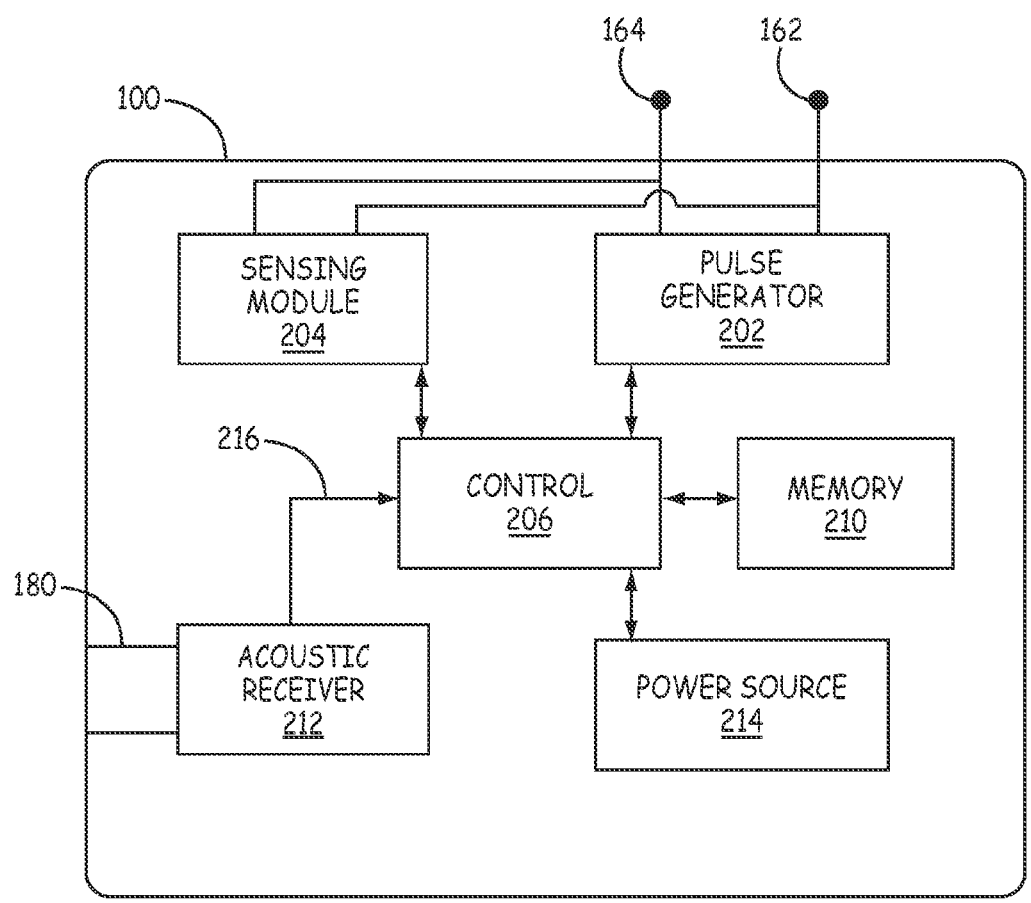
FIG. 11 is a functional block diagram of an example configuration of a triggered pacemaker.

FIG. 11 is a functional block diagram of an example configuration of pacemaker 100 (or pacemaker 500). Pacemaker 100 includes a pulse generator 202, a sensing module 204, a control module 206, memory 210, acoustic receiver 212 and a power source 214. Pulse generator 202 generates electrical stimulation pulses that are delivered to heart tissue via electrodes 162 and 164. Control module 206 controls pulse generator 202 to deliver a stimulation pulse in response to receiving a trigger detect signal 216 from acoustic receiver 212. In other embodiments, pulse generator 202 may be configured to receive trigger detect signal 216 directly from acoustic receiver 212 and deliver a stimulation pulse in response thereto. For example, a switch responsive to trigger detect signal 216 produced by acoustic receiver 212 may enable pulse generator 202 to produce a stimulation pulse that is applied to electrodes 162 and 164.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from acoustic receiver 212. Upon receiving the trigger detect signal 216 from acoustic receiver 212, control module 206 controls pulse generator 202 to couple the charged capacitor(s) to pacing electrodes 162, 164 to discharge the capacitor voltage and thereby deliver the pacing pulse. Alternatively, the trigger detect signal 216 causes control module to signal pulse generator 202 to initiate pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in pacemaker 100 for charging a pacing capacitor to a predetermined pacing pulse amplitude under the control of control module 202 and delivering a pacing pulse. Alternatively, pulse generator 202 may include a switch that connects power source 214 to pacing electrodes 162 and 164 to deliver the pacing pulse when a trigger detect signal 216 is produced by acoustic receiver 212.

Acoustic receiver 212 receives acoustic signals through coupling member 180. Acoustic receiver 212 includes a transducer comprising one or more piezoelectric crystal or piezoelectric ceramic transducer elements that are mounted directly along an inner surface of coupling member 180 and optionally along the battery subassembly 160 (FIG. 6A), for example according to any of the embodiments described above. Sound waves striking the piezoelectric transducer via coupling member 180 (and battery subassembly 160 in some examples) cause the transducer to produce a voltage signal (s) which is(are) passed to a comparator included in receiver 212 (or control module 206) for comparing to a trigger detection threshold. If a voltage signal produced by the piezoelectric transducer is greater than the detection threshold, a trigger detect signal 216 is passed to the pulse generator 202, directly or via control module 206, to cause pacing pulse delivery.

The individual voltage signals produced by multiple piezoelectric transducer elements may be summed, for example, for comparison to a trigger detection threshold or the largest voltage signal produced by a transducer may be compared to the detection threshold. In some embodiments, multiple piezoelectric transducer elements may be included that are responsive to different frequency bandwidths. Providing detection of different signal frequencies may enable different trigger signals to be transmitted for causing pacemaker 100 to perform different pacing functions. For example, detection of different trigger signals may cause different numbers of pacing pulses to be delivered, different pacing timing intervals to be set in response to the detected trigger signal, a different pulse amplitude and/or width to be used for delivering a pacing pulse, a pacing threshold search to be performed etc.

When control module 206 receives a trigger detect signal 216, control module 206 controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving a trigger detect signal 216, either directly from acoustic receiver 212 or via control module 206. In other examples, control module 206 may apply a delay time between receiving trigger detect signal 216 and enabling pulse generator 202 to deliver a pacing pulse.

The acoustic receiver 212 is configured to detect only the device-generated acoustical signal in some embodiments. In other words, acoustic receiver 212 may not be configured to sense and process any physiological acoustical signals for determining a physiological event, condition or state. Acoustic receiver 212 is tuned to detect acoustic signals in the range of the device-generated trigger signal but not in a range of typical physiological signals.

In some examples, pacemaker 100 is solely a therapy delivery device without sensing capabilities. In other examples, pacemaker 100 may include a sensing module 204 coupled to electrodes 162 and 164 for sensing near-field EGM signals for use in controlling the delivery of pacing pulses. Near-field EGM signals are cardiac event signals occurring in the heart chamber in which pacemaker 100 is implanted. For example, when pacemaker 100 is implanted in the LV, R-waves in the LV may be sensed by sensing module 204. Sensing module 204 generates an R-wave sense event signal that is provided to control module 206. Control module 206 may start a pacing timing interval upon receiving a trigger detect signal 216 from acoustic receiver 212. If an R-wave sense event signal is received by control module 206 from sensing module 204 prior to the pacing timing interval expiring, no pacing pulse is delivered by pulse generator 202. If the pacing timing interval expires prior to receiving an R-wave sense event signal from sensing module 204, control module 206 enables pulse generator 202 to deliver a pacing pulse. In this way, control module 206 may inhibit a scheduled pacing pulse in response to a sensed near-field cardiac event, e.g., a sensed R-wave or P-wave.

The pacing timing interval may be, for example, a VV interval to control delivery of a pacing pulse to the LV (or RV) relative to an intrinsic R-wave sensed by ICD 14. The pacing timing interval may be an AV interval to control delivery of a pacing pulse in a ventricle relative to an intrinsic P-wave sensed by ICD 14. The pacing timing interval may be relative to a pacing pulse that is delivered in another heart chamber that may also be delivered by another leadless intracardiac pacemaker that is triggered to deliver a pacing pulse by an acoustical trigger signal from emitting device 18. For example, ICD 14 may control emitting device 18 to produce an acoustical trigger signal. A pacing pulse may be delivered in one heart chamber by a first intracardiac pacemaker immediately upon detecting the acoustical trigger signal. A pacing pulse may be delivered by a second intracardiac pacemaker in a second heart chamber upon expiration of a pacing timing interval that is started upon detecting the acoustical trigger signal as long as the sensing module does not produce an intrinsic sensed event signal prior to the expiration of the pacing timing interval.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. Control module 206 may also be configured to perform diagnostic testing of pacemaker 100, which may include monitoring the remaining charge of power source 214. The connections between power source 214 and other pacemaker modules and components are not shown in FIG. 11 for the sake of clarity.

Circuitry represented by the block diagram shown in FIG. 11 may include any discrete and/or integrated electronic circuit components that implement analog and/or digital circuits capable of producing the functions attributed to pacemaker 100 herein. The functions attributed to pacemaker 100 (and pacemaker 500) herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of pacemaker 100 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by a processor of control module 206, cause pacemaker 100 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal detected by acoustic receiver 212

In one embodiment, pacemaker 100 includes only acoustic receiver 212, pulse generator 202 including low voltage charging circuitry and a pacing capacitor, power source 214 and control module 206 implemented as a logic circuit for controlling pacing pulse delivery in response to trigger signal detection. In this instance, pacemaker 100 is minimized in size and functionality and does not include sensing module 204 for receiving physiological signals.

Figure 12:
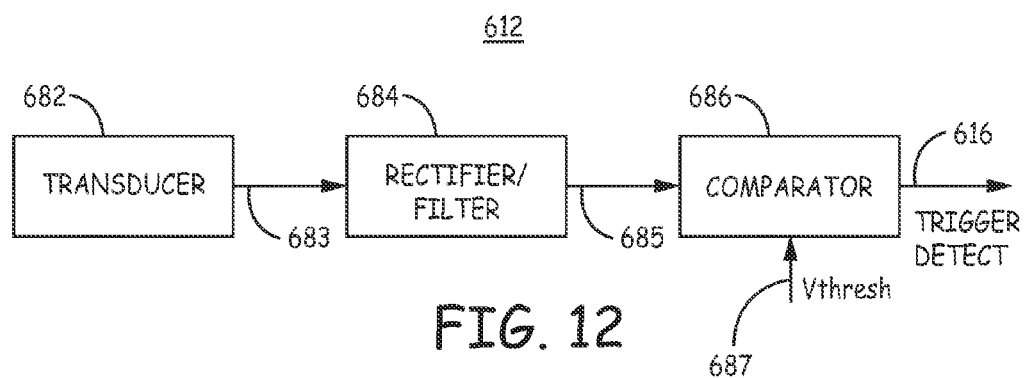
FIG. 12 is a block diagram of one example of an acoustic receiver included in a triggered pacemaker.

FIG. 12 is a block diagram of one example of an acoustic receiver 612 that may be included in a triggered therapy delivery device, such as pacemaker 100. Acoustic receiver 612 includes a transducer 682, which may include one or more piezoelectric crystal or piezoelectric ceramic elements. Transducer 682 produces an electrical output signal 683 when subjected to an acoustical signal. Transducer 682 may have a relatively narrow or wide bandwidth characterized by a center frequency that approximately matches the center frequency of the transducer included in the acoustical trigger signal emitting device (e.g., transducer 46 of emitting device 18 shown in FIG. 4). A rectifier and filter circuit 684 receives the electrical output signal 683 to produce a rectified and filtered signal 685 correlated to the acoustic signal converted by transducer 682. The rectified and filtered signal 685 is provided as input to comparator 686. Comparator 686 receives a detection threshold signal Vthresh 687 that is compared to rectified and filtered signal 685. When signal 685 exceeds Vthresh 687, a trigger detect signal 616 is produced and passed to the pacemaker control module 206 (or directly to the pulse generator 202) for triggering pacing pulse delivery.

Figure 13:
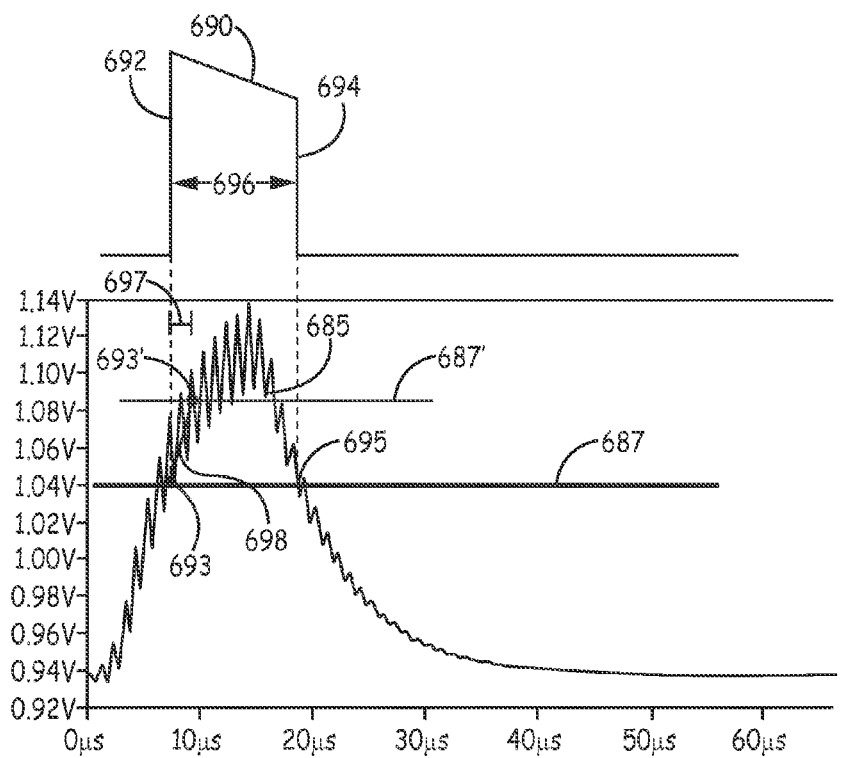
FIG. 13 is a plot of a rectified and filtered transducer signal provided to a comparator for detecting an acoustical trigger signal.

FIG. 13 is a plot of a rectified and filtered voltage signal 685 provided to comparator 686. When signal 685 crosses Vthresh 687, the pacemaker pulse generator 202 delivers pacing pulse 690 by discharging the pacing capacitor through the pacing electrodes 162 and 164. The leading edge 692 of pulse 690 starts upon the rising Vthresh crossing 693 of signal 685 in one example. In other examples, the pacemaker 100 may be configured to start the leading edge 692 after a time delay following rising Vthresh crossing 693.

The pacing capacitor is discharged until the signal 685 falls below the Vthresh 687 at Vthresh crossing 695 in this example. The pulse 690 may be terminated as soon as the signal 685 falls below Vthresh 687 at crossing 695 by disconnecting the pacing capacitor from the pacing electrodes 162 and 164 so that trailing edge 694 terminates pulse 690 at a pulse width 696 that is approximately equal to the time interval that signal 685 exceeds Vthresh 687. In other examples, trailing edge 694 occurs at a predetermined time delay after the falling Vthresh crossing 695 so that pacing pulse 690 is delivered with a predetermined pulse width that may be different than the time interval that signal 685 exceeds Vthresh 687. In other examples, the signal 685 may include multiple pulses crossing Vthresh 687 multiple times in a pulse pattern that is detected by acoustic receiver 612 as a valid trigger signal.

In another embodiment, a second threshold 687' in addition to Vthresh 687 may be added to determine a time interval 697 between a first threshold crossing 693 and a second threshold crossing 693' of trigger signal 685. This time interval 697 is used by pacemaker 100 to determine a rising (and/or falling slope) of the trigger signal 685. The determined slope 698 may be used to validate a detected trigger signal, distinguish between mutually exclusive trigger signals intended for different therapy delivery devices when multiple therapy delivery devices are implanted, and/or encode a pacing pulse parameter setting in the trigger signal. When slope 698 is used to validate trigger signal 685, leading edge 692 of pacing pulse 696 may be delayed in time from the first and second threshold crossings 693 and 693', e.g., by setting a pacing timing interval upon first threshold crossing 693) to allow verification time by control module 206 of the trigger signal 685. If trigger signal 685 is not validated based on slope 698, the scheduled pacing pulse may be cancelled.

Figure 14:
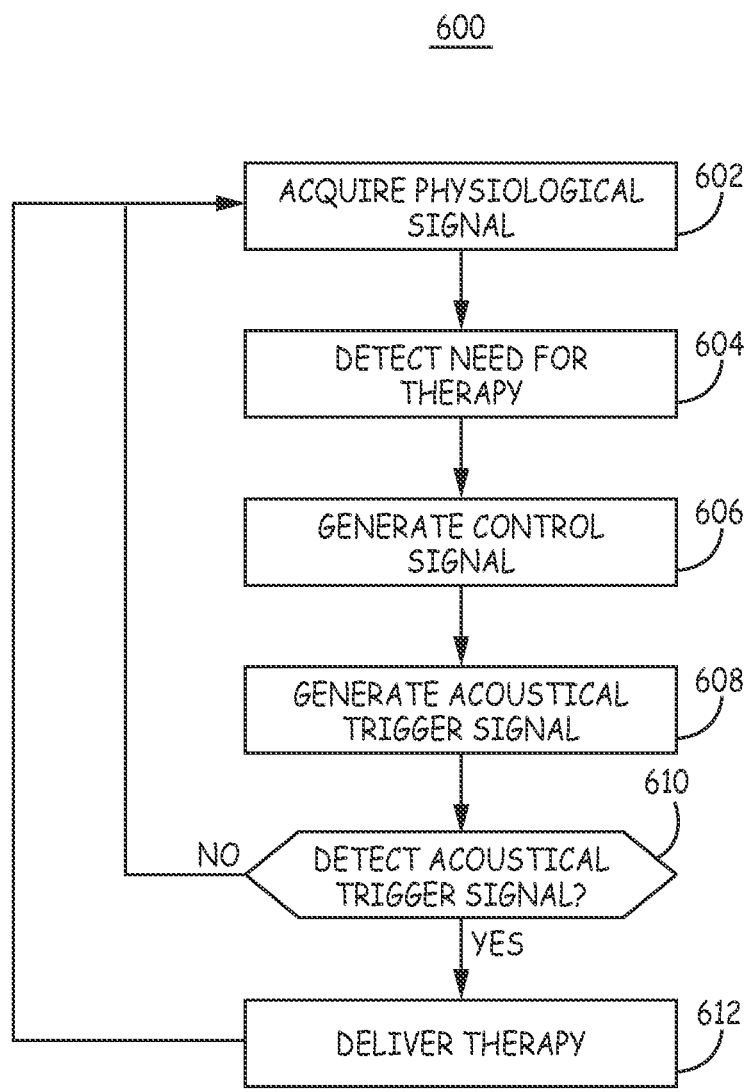
FIG. 14 is a flow chart of a method for controlling a triggered therapy delivery device according to one example.

FIG. 14 is a flow chart 600 of a method for controlling a triggered therapy delivery device according to one example. At block 602, a sensing device, e.g., sensing device 4 (FIGS. 1 and 1A) or ICD 14 (FIG. 2A), acquires one or more physiological signal, e.g., an ECG signal, pressure signal, heart sound signal, or other physiological signal, for sensing events or conditions that indicate a need for automatic therapy delivery. The sensing device detects a need for therapy, at block 604, based on the sensed physiological signal(s). The sensing device need not be directly electrically coupled to the triggered therapy delivery device, e.g., therapy delivery device 6 of FIG. 1A or pacemaker 100 of FIG. 2A. The sensing device generates a control signal at block 606 that is passed directly to the acoustical emitting device, e.g., device 5, 18 or 60 shown in FIG. 1A, 2A or 2B respectively, that is in wired connection with the sensing device. Alternatively the sensing device generates a control signal that is encoded by a telemetry communication module and transmitted wirelessly to the acoustical emitting device at block 606.

The emitting device generates an acoustical trigger signal at block 608 in response to receiving the control signal. The triggered therapy delivery device receives the acoustical trigger signal at block 610. In response to detecting the acoustical trigger signal, a therapy is automatically delivered at block 612 by the therapy delivery device. If no acoustical trigger signal is detected, the sensing device continues to monitor the physiological signal at block 604.

Figure 15:
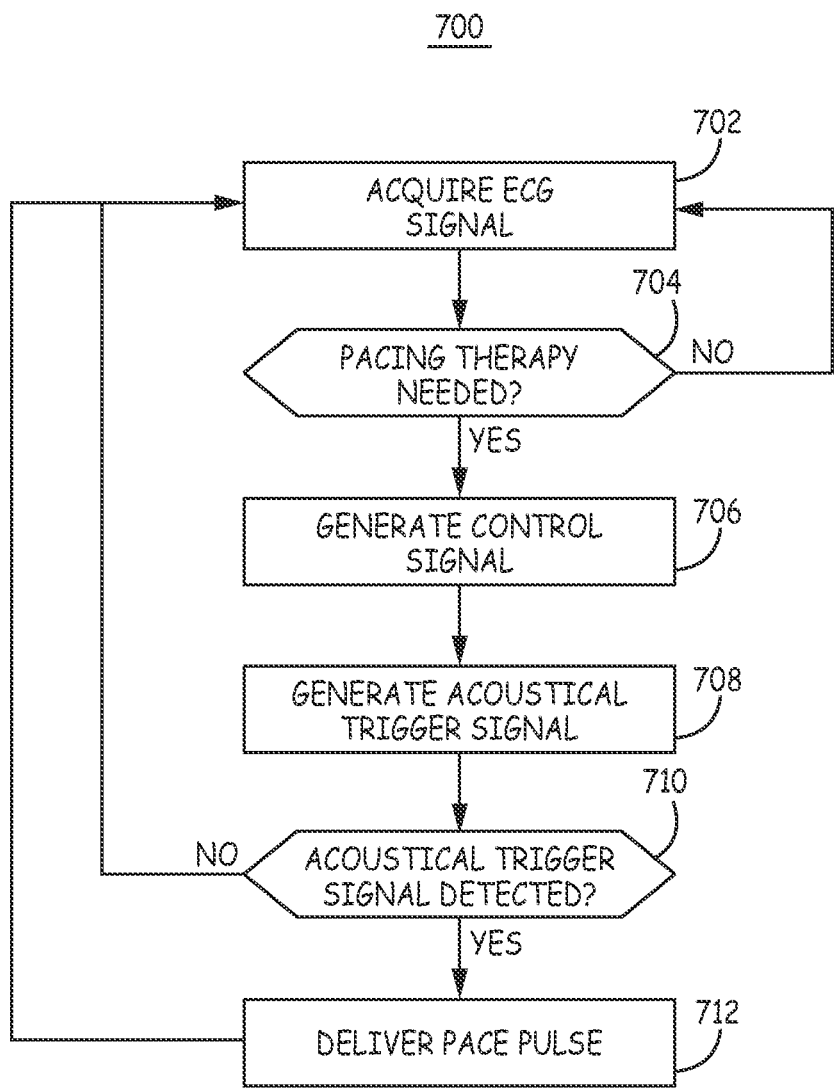
FIG. 15 is a flow chart of a method for controlling a cardiac pacing therapy delivered by a triggered pacemaker.

FIG. 15 is a flow chart 700 of a method for controlling a cardiac pacing therapy automatically delivered by a triggered pacemaker 100. A sensing device 4 or 14 acquires an ECG signal at block 702. The sensing device may be configured as a sensing-only device (e.g., sensing device 4 as shown in FIG. 1B) for monitoring the ECG signal using electrodes carried on the sensing device 4 and/or a lead extending from the sensing device 4. The sensing device may or may not be capable of delivering a therapy. In one example, the sensing device includes cardioversion/defibrillation capabilities for treating tachyarrhythmias, such as ICD 14 shown in FIG. 2A. As described above, the sensing device may be configured to monitor the ECG to detect a need for pacing and for detecting VT and VF and delivering shock therapies as needed. The sensing device may be an extrathoracic device, e.g., implanted in a subcutaneous or submuscular pocket, or an intrathoracic device and need not be in wired connection with the pacemaker 100.

If a pacing therapy is needed, as determined at block 704 based on the sensed ECG signal, a control signal 95 is generated by the sensing device at block 706. The control signal 95 may be an electrical signal passed directly to the acoustical emitting device (e.g., emitting device 5, 18 or 60, either through a wired connection or via conversion and transmission of a wireless telemetry signal such as an RF communication signal.

The acoustical emitting device generates an acoustical trigger signal at block 708 in response to receiving the control signal from the sensing device. If the pacemaker 100 detects an acoustical trigger signal, as determined at block 710, one or more pacing pulses are delivered at block 712 in response to the trigger signal detection. If no acoustical trigger signal is detected, the sensing device 4 or 14 continues monitoring the ECG signal for the need for a pacing pulse(s).

The control signal 95 originating from the sensing device 4 or 14 is not an acoustical signal in some examples since more electrically efficient signals may be used for triggering the emitting device 5,18 or 60 to emit an acoustical signal. In other examples, the sensing device 4 or 14 may pass an acoustical control signal to the emitting device 5, 18 or 60 that acts as an acoustical relay device. The acoustical relay device may alternate between send and receive modes where it receives an acoustical control signal from the sensing device 4 or 14 then sends the acoustical trigger signal on to the pacemaker 100.

Figure 16:
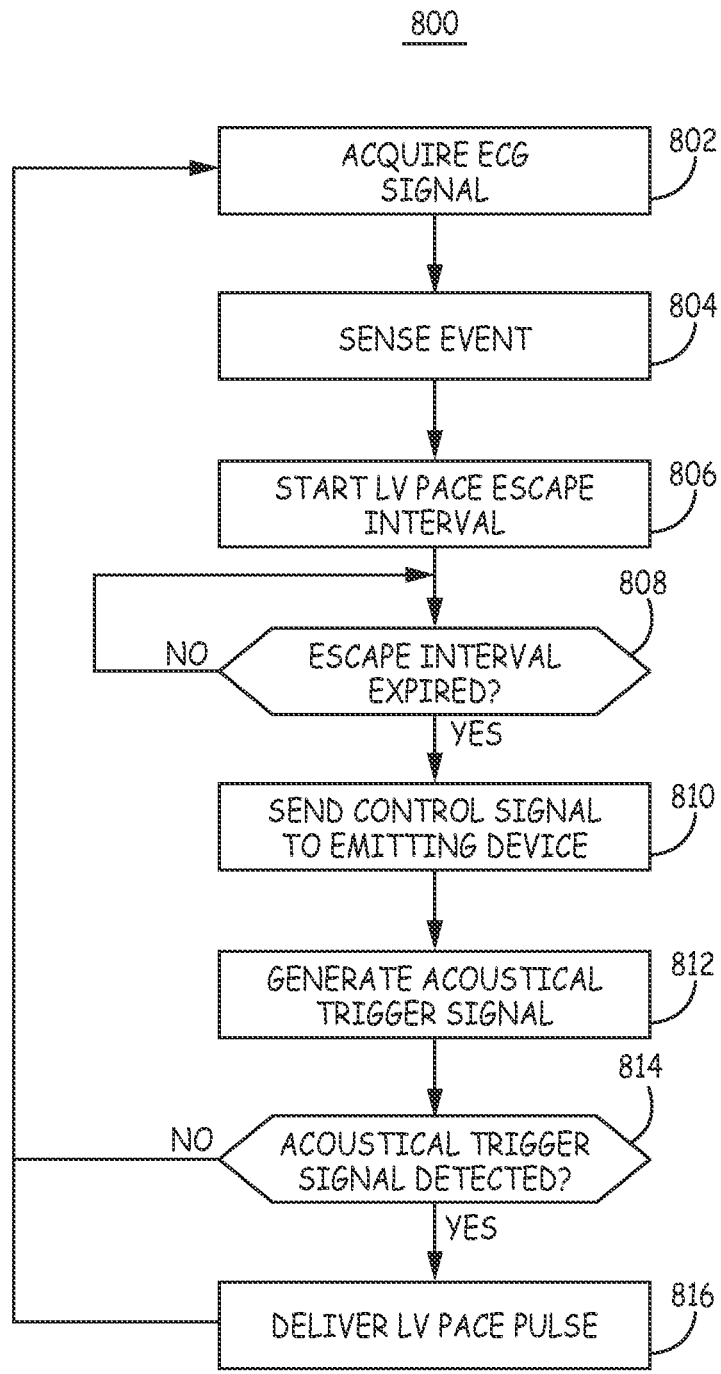
FIG. 16 is a flow chart of a method for controlling cardiac resynchronization therapy (CRT) delivered by a triggered pacemaker according to one embodiment.

FIG. 16 is a flow chart 800 of a method for controlling cardiac resynchronization therapy (CRT) according to one embodiment. At block 802, a sensing device 4 or 14 receives an ECG signal for sensing P-waves and/or R-waves attendant to the depolarization of the atria and the ventricles, respectively. The sensing device may be a sensing-only device 4 as shown in FIG. 1B or an ICD 14, e.g., as shown in FIG. 2A and FIG. 3. A timing event, i.e., a P-wave or an R-wave, is sensed at block 804 causing a pacing escape interval to be started in the sensing device 4 or 14. In the example shown, an LV pacing escape interval is started at block 806. The LV pacing escape interval may be based on the onset of a sensed R-wave, a sensed P-wave, or other time point identified on the ECG signal at block 804.

If the pacing escape interval expires (block 808), a control signal 95, as shown in FIG. 4, is produced by the sensing device 4 or 14 and sent to the acoustical trigger signal emitting device 5, 18 or 60 at block 810. The control signal 95 produced by the sensing device 4 or 14 may be an electrical signal sent to the emitting device 5, 18 or 60 by a wired conductor coupling the sensing device 4 or 14 to the emitting device 5, 18 or 60. As described above, the emitting device 5 or 18 may be housed within or along the sensing device 4 or 14 or a connector block. Alternatively the emitting device 18 or 60 may be carried by a lead coupled to the sensing device 4 or 14.

In other examples, the control signal produced by the sensing device 4 or 14 is converted to a wireless telemetry communication signal that is transmitted to a receiver included in the emitting device. The emitting device may be a leadless device implanted away from the sensing device or may be carried by a lead extending from the sensing device 4 or 14 but configured to receive wireless telemetry signals, such as RF signals.

At block 812, the emitting device generates an acoustical trigger signal upon receiving the control signal from the sensing device 4 or 14. An intracardiac pacemaker 100 implanted in the LV is configured to detect the acoustical trigger signal. If an acoustical trigger signal is detected by the pacemaker 100, as determined at block 814, the pacemaker 100 delivers an LV pacing pulse at block 816. If no acoustical trigger signal is detected, the sensing device 4 or 14 continues to sense events from the ECG signal for controlling pacing timing intervals and generating control signals as needed.

Figure 17:
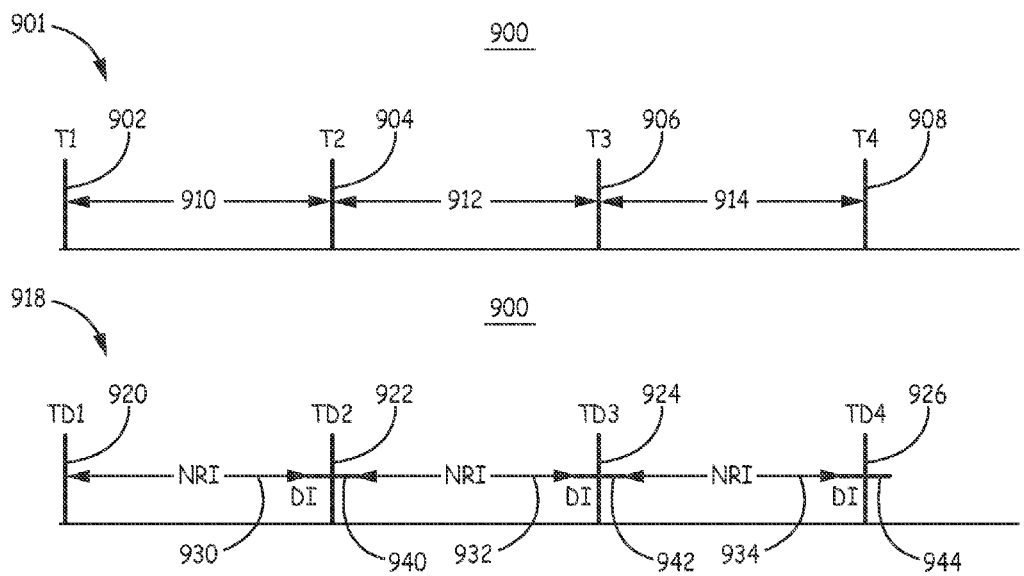
FIG. 17 is a timing diagram depicting a trigger signal emitted by an emitting device and the corresponding trigger signal detection by a triggered therapy delivery device.

FIG. 17 is a timing diagram 900 depicting a trigger signal 901 emitted by an emitting device and the corresponding trigger detect signal 918 produced by the acoustic receiver, e.g., acoustic receiver 212, of a triggered therapy delivery device, e.g., pacemaker 100. In various embodiments, trigger signal 901 may include two or more pulses (T1 through T4) 902, 904, 906 and 908 that are each emitted at a desired operating frequency, e.g., 1 MHz, for a desired pulse width. The trigger signal pulses 902, 904, 906, and 908 are sent at predetermined pulse intervals 910, 912 and 914, which are shown to be equal pulse intervals in FIG. 17 but may be unequal intervals as defined by predetermined inter-pulse intervals according to a specified trigger signal pattern.

Detection of the first trigger signal pulse 902 by the therapy delivery device causes the acoustic receiver of the therapy delivery device to produce a trigger detect signal (TD1) 920. The TD signal 920 causes the receiver to start a noise rejection interval (NRI) 930. If any trigger signal pulses are detected during the NRI 930, the first TD signal 920 is rejected as noise detection. The next time a trigger pulse is detected, the acoustic receiver will restart the NRI 930.

If no trigger signal pulses are detected during NRI 930, a valid detection interval (DI) 940 is started upon expiration of the NRI 930. If a trigger signal pulse 904 is detected during DI 940, the two TD signals 920 and 922, separated by a NRI 930 absent of any TD signals, are identified as a valid trigger signal pulses. The two TD signals 920 and 922 produced by the acoustic receiver are used by the therapy delivery device control module 206 in detecting a valid trigger signal.

The valid TD signal 922 causes a new NRI 932 to be started at the expiration of the DI 940. The next NRI 932 may be equal or unequal to the first NRI 930, depending on the known, predetermined interpulse intervals 910, 912 and 914 of the trigger signal 901. Any pulses detected during NRI 932 will be rejected as noise and both TD1 920 and TD2 922 may be rejected as noise. The next time a pulse is detected by the acoustic receiver, the first NRI 930 may be restarted.

If the next NRI 932 expires without a TD signal, a valid DI 942 is started. A TD signal 924 produced by the acoustic receiver in response to the third trigger signal pulse 906 during the valid DI 942 is an indication of a valid trigger signal 901. At the expiration of the DI 942, a third NRI 934 is started, followed by a DI 944 if no pulses are detected during the third NRI 934. A fourth trigger signal pulse 908 is detected during the DI 944 as a valid trigger signal pulse.

In this example, a valid trigger signal 901 includes four pulses 902 through 908 at the specified intervals 910 through 914. A valid trigger signal may be defined having another number of pulses greater than or less than four. In the illustrative example, the valid trigger signal 901 is detected by the acoustic receiver after four consecutive TD signals 920 through 926 are detected during the four valid detection intervals 940, 942 and 944 with no trigger detection signals during the NRIs 930, 932 and 934. In response to detecting the valid trigger detect signals 920 through 926, the therapy delivery device 100 will deliver a pacing pulse. In this way, trigger signals can be reliably detected for trigging the therapy delivery device 100 in the presence of acoustical noise, such as during ultrasound imaging procedures.

Thus, various examples of a medical device system including an acoustically triggered therapy delivery device and associated method for triggering the therapy delivery device to delivery therapy to a patient have been described according to illustrative embodiments. However, one of ordinary skill in the art will appreciate that various modifications may be made to the described embodiments without departing from the scope of the following claims.

The invention claimed is:

1. A medical device system for automatically delivering a therapy, comprising:
   a first device configured to sense a physiological signal and generate a control signal in response to the physiological signal;
   an acoustical emitting device controlled by the first device to emit an acoustical trigger signal in response to receiving the control signal from the first device; and a second device comprising:
  a transducer for receiving the acoustical trigger signal,
  a therapy delivery module, and
  a power source comprising at least one battery connected to the therapy delivery module and configured to supply power required by the therapy delivery module;
  the second device configured to detect the acoustical trigger signal and deliver the therapy to a patient in response to detecting the acoustical trigger signal, wherein delivering the therapy comprises enabling the power source connected to the therapy delivery module of the second device to provide power to deliver the therapy.

2. The system of claim 1, wherein:
the first device is configured to sense cardiac electrical signals via a plurality of electrodes coupled to the first device; and
the second device is configured to deliver an electrical stimulation pulse to a targeted body tissue of the patient via an electrode pair coupled to the second device in response to detecting the acoustical trigger signal.

3. The system of claim 1, wherein the second device is wholly implantable within a heart chamber.

4. The system of claim 1, wherein the first device comprises a housing and the acoustical emitting device is enclosed by the housing,
the housing further comprising an acoustical coupling member for acoustically coupling the acoustical trigger signal with adjacent body tissue,
the acoustical emitting device configured to emit the acoustical trigger signal through the coupling member.

5. The system of claim 1, further comprising a medical lead extending from the first device, the acoustical emitting device comprising a torus ultrasound transducer carried by the medical lead.

6. The system of claim 1, wherein:
the acoustical emitting device comprises a drive signal circuit and a plurality of emitting transducers;
wherein the first device is configured to control the drive signal circuit to activate the plurality of emitting transducers to at least one of focus a plurality of emitted acoustical signals toward the second device and emit the plurality of acoustical signals to constructively interfere.

7. The system of claim 1, wherein the second device comprises an acoustic coupling member through which the transducer receives the trigger signal, the coupling member extending along at least one side of the second device.

8. The system of claim 7, wherein:
the transducer comprises a plurality of piezoelectric elements extending along the coupling member;
the second device comprises an acoustical receiver configured to:
  receive a voltage signal from each of the plurality of piezoelectric elements;
  compare the voltage signals to a detection threshold; and
  detect the trigger signal in response to the detection threshold being exceeded.

9. The system of claim 1, wherein the second device comprises a faceted coupling member through which the transducer receives the trigger signal.

10. The system of claim 9, wherein the faceted coupling member comprises a plurality of facets at least partially circumscribing the second device.

11. The system of claim 1, wherein the therapy delivery module comprises at least one capacitor,
the second device further configured to charge at least one capacitor of the therapy delivery module from the power source prior to detecting the acoustical trigger signal, wherein delivering the therapy in response to detecting the acoustical trigger signal comprises discharging the at least one capacitor charged prior to detecting the acoustical trigger signal.

12. The system of claim 1, wherein the therapy delivery module is coupled to pacing electrodes and comprises a switch that connects the power source to the pacing electrodes,
wherein delivering the therapy in response to detecting the acoustical trigger signal comprises enabling the switch to connect the power source to the pacing electrodes to deliver a pacing pulse in response to detecting the acoustical trigger signal.

13. A method for delivering an automatic therapy by a medical device system, comprising:
sensing a physiological signal by a first device;
generating a control signal by the first device in response to the physiological signal;
automatically emitting an acoustical trigger signal by an acoustical emitting device receiving the control signal;
detecting the acoustical trigger signal by a second device comprising a transducer that is responsive to the acoustical trigger signal; and
delivering the therapy to a patient in response to the second device detecting the acoustical trigger signal, wherein delivering the therapy comprises enabling a power source of the second device comprising at least one battery and being connected to a therapy delivery module of the second device to provide power to deliver the therapy.

14. The method of claim 13, wherein the physiological signal is a cardiac electrical signal sensed using a plurality of electrodes coupled to the first device,
wherein delivering the therapy in response to detecting the acoustical trigger signal comprises delivering an electrical stimulation pulse generated by the second device to a targeted body tissue of the patient using an electrode pair coupled to the second device.

15. The method of claim 13, further comprising transmitting the acoustical trigger signal from the emitting device to the second device wholly implanted within a heart chamber.

16. The method of claim 13, wherein emitting the acoustical trigger signal comprises emitting the acoustical trigger signal through a coupling member of a housing of the first device, the acoustical coupling member coupling the acoustical trigger signal with adjacent body tissue.

17. The method of claim 16, further comprising receiving the acoustical trigger signal by the transducer through a coupling member extending along at least one side of the second device.

18. The method of claim 17, further comprising:
receiving by an acoustical receiver a voltage signal from each of a plurality of piezoelectric elements extending along the coupling member;
comparing the voltage signals to a detection threshold; and
detecting the trigger signal in response to the detection threshold being exceeded.

19. The method of claim 16, further comprising receiving the acoustical trigger signal by the transducer through a faceted coupling member.

20. The method of claim 16, further comprising receiving the acoustical trigger signal through a coupling member having a faceted portion extending along less than a circumference of the second device.

21. The method of claim 13, wherein emitting the acoustical trigger signal comprises activating a torus ultrasound transducer carried by a medical extending from the first device.

22. The method of claim 13, further comprising controlling a drive signal circuit of the acoustical emitting device by the first device to activate a plurality of emitting transducers to at least one of focus a plurality of emitted acoustical signals toward the second device and emit the plurality of acoustical signals to constructively interfere.

23. A non-transitory, computer-readable storage medium storing a set of instructions that, when executed by a processor of an implantable medical device system, cause the system to:

sense a physiological signal by a first device;

generate a control signal by the first device in response to the physiological signal;

emit an acoustical trigger signal by an acoustical emitting device in response to the control signal;

detect the acoustical trigger signal by a second device comprising a transducer that is responsive to the acoustical trigger signal; and deliver a therapy by the second device to a patient in response to the second device detecting the acoustical trigger signal, wherein delivering the therapy comprises enabling a power source of the second device comprising at least one battery and being connected to a therapy delivery module of the second device to provide power to deliver the therapy.

* * * * *